United States Patent
Kim et al.

(10) Patent No.: US 9,644,183 B2
(45) Date of Patent: May 9, 2017

(54) METHOD FOR DIFFERENTIATION OF STEM CELLS INTO VASCULAR CELLS AND THE INDUCTION OF ANGIOGENESIS USING THE SAME

(75) Inventors: Sang-Heon Kim, Seoul (KR); Soo Hyun Kim, Seoul (KR); In Su Park, Seoul (KR); Young Mee Jung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 344 days.

(21) Appl. No.: 13/259,767

(22) PCT Filed: Mar. 24, 2010

(86) PCT No.: PCT/KR2010/001807
§ 371 (c)(1),
(2), (4) Date: Sep. 23, 2011

(87) PCT Pub. No.: WO2010/110596
PCT Pub. Date: Sep. 30, 2010

(65) Prior Publication Data
US 2012/0134965 A1    May 31, 2012

(30) Foreign Application Priority Data

Mar. 24, 2009  (KR) .................. 10-2009-0024681
Jan. 11, 2010  (KR) .................. 10-2010-0002149

(51) Int. Cl.
| | | |
|---|---|---|
| C12N 5/071 | (2010.01) | |
| A61K 35/545 | (2015.01) | |
| A61K 35/28 | (2015.01) | |
| A61K 35/30 | (2015.01) | |
| A61K 35/51 | (2015.01) | |
| A61K 35/44 | (2015.01) | |

(52) U.S. Cl.
CPC ............. *C12N 5/069* (2013.01); *A61K 35/28* (2013.01); *A61K 35/30* (2013.01); *A61K 35/44* (2013.01); *A61K 35/51* (2013.01); *A61K 35/545* (2013.01); *C12N 2501/115* (2013.01); *C12N 2506/1384* (2013.01); *C12N 2513/00* (2013.01); *C12N 2533/52* (2013.01); *C12N 2533/54* (2013.01); *C12N 2533/70* (2013.01)

(58) Field of Classification Search
CPC .. C12N 5/00; C12N 55/0662; C12N 55/0667; C12N 55/069; C12N 2513/00; C12N 2533/00; C12N 5/069; A61K 35/28; A61K 35/35; A61K 38/1825; A61K 35/545; A61K 35/30; A61K 35/51; A61K 35/44
See application file for complete search history.

(56) References Cited

U.S. PATENT DOCUMENTS

| | | |
|---|---|---|
| 6,777,231 B1 | 8/2004 | Katz et al. |
| 2005/0227353 A1 | 10/2005 | Mummery |
| 2007/0128171 A1* | 6/2007 | Tranquillo et al. .......... 424/93.7 |
| 2008/0025955 A1 | 1/2008 | Nakao et al. |

FOREIGN PATENT DOCUMENTS

| | | |
|---|---|---|
| EP | 2088190 | 8/2009 |
| WO | 2008/056779 | 5/2008 |
| WO | WO 2008/056779 | 5/2008 |

OTHER PUBLICATIONS

Lin et al. Expression of CD34 in endothelial cells, hematopoietic progenitors and nervous cells in fetal and adult mouse tissues. Eur. J. Immunol. 1995.25: 1508-1516.*
BD BioCoat Cellware. 2002. BD Biosciences p. 1-23.*
Bunnell et al. Adipose-derived stem cells: Isolation, expansion and differentiation. Methods 45 (2008) 115-120.*
Phinney et al. Plastic Adherent Stromal Cells From the Bone Marrow of Commonly Used Strains of Inbred Mice: Variations in Yield, Growth, and Differentiation. Journal of Cellular Biochemistry 72:570-585 (1999).*
Liu et al. Flk-1+ Adipose-Derived Mesenchymal Stem Cells Differentiate into Skeletal Muscle Satellite Cells and Ameliorate Muscular Dystrophy in mdx Mice. Stem Cells and Development 16:695-706 (2007).*
Shaw et al. Hematopoietic stem cells and endothelial cell precursors express Tie-2, CD31 and CD45. Blood Cells, Molecules, and Diseases 32 (2004) 168-175.*
Quarto et al. FGF-2 Inhibits Osteogenesis in Mouse Adipose Tissue-Derived Stromal Cells and Sustains their Proliferative and Osteogenic Potential State. Tissue Engineering vol. 12, No. 6, 2006 p. 1405-1418.*
Ishihara et al. Heparin-carrying polystyrene (HCPS)-bound collagen substratum to immobilize heparin-binding growth factors and to enhance cellular growth. J Biomed Mater Res 56: 536-544, 2001.*
Geuijen et al.Identification and Characterization of Heparin Binding Regions of the Fim2 Subunit of Bordetella pertussis. Infect. Immun. 1998, 66(5):2256-63.*
Lemaitre et al. Production and purification of active FGF2 via recombinant fusion protein. Biochimie (1995) 77, 162-166.*
Park et al. The correlation between human adipose-derived stem cells differentiation and cell adhesion mechanism. Biomaterials 30 (2009) 6835-6843.*
Kang et al. Neurogenesis of Rhesus adipose stromal cells. Journal of Cell Science 117 (18): 4289-4299.*

(Continued)

*Primary Examiner* — Taeyoon Kim
(74) *Attorney, Agent, or Firm* — Goldilocks ZONE IP Law

(57) ABSTRACT

A method for differentiating stem cells into vascular cells, including adhering the stem cells to a culture plate with a surface having a hydrophobic property or on which a growth factor is immobilized, and culturing the cells. The cultured stem cells later detach from the culture plate as their density increases to form a three-dimensional cell cluster and differentiate into vascular cells. The cell cluster can be used as a cell therapy agent for angiogenesis.

7 Claims, 14 Drawing Sheets

(56) References Cited

OTHER PUBLICATIONS

Nunclon® cell culture dishes. Sigma-Aldrich product information. downloaded on Jul. 31, 2014 from http://www.sigmaaldrich.com/catalog/product/sigma/d7804?lang=en&region=US. p. 1-2.*
B. Cousin et al., "Reconstitution of Lethally Irradiated Mice by Cells IUsolated from Adipose Tissue," BBRC 301: 1016, 2003.
Miranville et al., "Improvement of Postnatal Neovascularization by Human Adipose Tissue-Derived Stem Cells," Circulation 110: 349, 2004.
S. Gronthos et al., "Surface Protein Characterization of Human Adipose Tissue-Derived Stromal Cells," J. Cell Physiol. 189: 54, 2001.
M.J. Seo et al., "Differentiation of Human Adipose Stromal Cells into Heptic Lineage in Vitro and in Vivo," BBRC 328: 258, 2005.
Martin Brzoska et al., "Epithelial Differentiation of Human Adipose Tissue-Derived Adult Stem Cells," BBRC 330: 142, 2005.
Ying Cao et al., "Human Adipose Tissue-Derived Stem Cells Differentiation Into Endothelial Cells in Vitro and improve Postnatal Neovascularization in Vivo," BBRC 332: 370, 2005.
Kristine M. Safford et al., "Neurogenic Differentiation of Murine and Human Adipose-Derived Derived Stromal Cells", BBRC 294: 371, 2005.
Rei Ogawa et al., "Adipogenic Differentiation by Adipose-Derived Stem Cells Harvested from GFP Transgenic Mice-Including Relationship of Sex Differences", BBRC 319: 511, 2004.
Rei Ogawa, et al., "Osteogenic and Chondrogenic Differentiation by Adipose-Derived Stem Cells Harvested from GFP Transgenic Mice", BBRC 313: 871, 2004.
Hani A. Awad et al., "Chondrogenic Differentiation of Adipose-Derived Adult Stem Cells in Agarose, Alginate, and Gelatin Scaffolds", Biomaterials 25: 3211, 2004.
Jun Fujimura et al., "Neural Differentiation of Adipose-Derived Stem Cells Isolated from GFP Transgenic Mice," BBRC 333: 116, 2005.
Cao Y et al., "Human Adipose Tissue-Derived Stem Cells Differentiate into Endothelial Cells in Vitro and Improve Postnatal Neovascularization in Vivo", Biochem. Biophys. Res. Commun. 332: 370-379, 2005.
Martinez-Estrada O.M. et al., "Human Adipose Tissue as a Source of Flk-1$^+$ cells: New Method of Differentiation and Expansion", Cardiovasc. Res. 65(2): 328-33, 2005.
International Search Report dated Jan. 10, 2011 in Int'l Appln. No. PCT/KR2010/001807.
Preliminary Report on Patentability dated Sep. 27, 2011 in Int'l Appln. No. PCT/KR2010/001807.

* cited by examiner

CD31/KDR/DAPI

CD34/CD31/DAPI

CD34/KDR/DAPI

α-SMA

MAP

Nestin

CD31/KDR/DAPI

CD34/CD31/DAPI

CD34/KDR/DAPI

METHOD FOR DIFFERENTIATION OF STEM CELLS INTO VASCULAR CELLS AND THE INDUCTION OF ANGIOGENESIS USING THE SAME

CROSS REFERENCE TO RELATED APPLICATIONS

This application claims the benefit of International Application No. PCT/KR2010/001807, filed Mar. 24, 2010, and claims the benefit of Korean Application No. 10-2009-0024681, filed Mar. 24, 2009, and Korean Application No. 10-2010-0002149, filed Jan. 11, 2010, the disclosures of all of which are incorporated herein by reference.

FIELD OF THE INVENTION

The present invention relates to a method for differentiation of stem cells into vascular cells by culturing stem cells in the form of a three-dimensional cell cluster and the use of the three-dimensional cell cluster for in vivo angiogenesis.

BACKGROUND OF THE INVENTION

Angiogenesis is the process of new blood vessel formation by degradation of extracellular matrix (ECM), migration, division, and differentiation by pre-existing vascular endothelial cells. Angiogenesis is involved in various physiological and pathological events, such as embryonic development, wound healing, tumor growth, chronic inflammation, obesity, etc. Angiogenesis includes the proliferation of vascular endothelial cells and their migration from the blood vessel wall to the surrounding tissue following the source of the angionenic stimuli. Sequentially, the activation of various proteases helps the vascular endothelial cells to degrade the basement membrane and form loops. These formed loops differentiate into new vessels.

The angiogenic process is known to be strictly regulated by various types of angiogenic simulators and inhibitors. Angiogenesis does not occur in a normal state due to a quantitative balance between angiogenic inhibitors, such as thrombospondin-1, platelet factor-4, angiostatin, etc., and angiogenic stimulators, such as vascular endothelial growth factor (VEGF), basic fibroblast growth factor (bFGF), etc. However, when a wound or tumor occurs, for the wound healing or tumor growth, the above balance is upset to enable new blood vessels to grow. The formation involves an overexpression of angiogenic stimulators.

Angiogenesis is an essential step for tissue regeneration, as well as wound healing. For example, a placenta in which angiogenesis is underdeveloped is an important cause of miscarriage. Necrosis, ulcer, and ischemia caused by non-formation of vessels cause malfunction of tissues or organisms, or can lead to death. In addition, atherosclerosis, myocardial infarction, and angina pectoris are due to an inadequate blood supply. Accordingly, treatment methods of reducing tissue damage caused by hypoxia or undernutrition due to incomplete blood vessel formation, while inducing or stimulating neovascularization for proper tissue regeneration, are needed.

A therapy of treating diseases using angiogenesis is called an angiogenic therapy. VEGF, an angiogenic simulator, is used as a therapeutic agent for severe local anemia. In addition, angiogenic simulators, such as FGF, epidermal growth factor (EGF) and platelet-derived endothelial growth factor (PDEGF), are also being studied for clinical treatment. However, the above factors are disadvantageous for clinical applications because they are proteins which are difficult and costly to isolate and purify.

In 1997, Asahara and colleagues reported that a purified population of $CD34^+$ hematopoietic progenitor cells isolated from the circulation system of adults could be in vitro differentiated into endothelial lineage cells named endothelial progenitor cells (EPCs). Based on the above, bone marrow-derived cells and EPCs proliferated ex vivo were used in the treatment of limb ischemia and the regeneration of heart muscles The EPCs were tried in auto-transplantation for blood vessel regeneration. After that, it was reported that not only stromal vascular fraction (SVF) in the adipose tissue but mesenchymal stem cells (MSCs) found in bone marrow and umbilical cord blood could also be differentiated into vascular endothelial cells. Adipose stem cells could be differentiated ex vivo into vascular endothelial cells and showed early angiogenesis activity in ischemia animal models.

However, because stem cells are individually transplanted in animal models of ischemia using MSCs, most reports so far have said that growth factors secreted from the stem cells, rather than the stem cells themselves, induce angiogenesis of the host. Some stem cells are introduced into the newly formed blood vessels but there have been no reports that stem cells per se induce angiogenesis. There has also been a report that when cells produced by decomposing adipose tissues were transplanted into animals without culturing the stromal vascular fraction (SVF) therefrom, it was possible to differentiate them into vascular endothelial cells. However, since the above method did not induce proliferation of adipose stem cells via subculturing, the amount of vascular endothelial cells differentiated from the adipose stem cells was very small. In particular, since the differentiated vascular endothelial cell showed low levels of proliferation and differentiation, the application is limited.

Therefore, the present inventors conducted extensive research on an angiogenic therapy using stem cells for effectively inducing angiogenesis of stem cells transplanted in the body. As a result, the present inventors found that, if stem cells are cultured on a culture plate with a surface of a hydrophobic property by physically attaching the cells to the culture plate via cell-matrix interactions, or they are cultured where they are bonded to growth factors immobilized to the surface of the culture plate via their interaction with the growth factors, stem cells proliferate while being attached to the surface of the culture plate initially, while the proliferated stem cells are later detached from the surface of the culture plate to form a three-dimensional cell cluster as the intercellular interaction becomes stronger than the cell-matrix interaction under high cellular density. The present inventors further discovered that the stem cells within the thus formed cell cluster not only secrete angiogenic stimulators, but are also differentiated into vascular cells. Based on the above findings, the present inventors developed a method of using a cell cluster composed of vascular cells differentiated from stem cells as a cell therapy agent for angiogenesis to achieve the present invention.

SUMMARY OF THE INVENTION

It is, therefore, an objective of the present invention to provide a method for differentiation of stem cells into vascular cells in high yields within a short period of time for the in vivo induction of angiogenesis using the stem cells, where the method comprises culturing stem cells in the form of a three-dimensional cell cluster.

It is another objective of the present invention to provide a cell therapy agent for vascular diseases or functional cells in a composite scaffold for use in tissue engineering comprising a three-dimensional cell cluster, where the three-dimensional cell cluster is composed of vascular cells differentiated from stem cells by the above method.

In order to achieve the above objectives, the present invention provides a method for the differentiation of stem cells into vascular cells comprising culturing stem cells by adhering them onto a culture plate with a surface having a hydrophobic property or a culture plate onto which a growth factor is immobilized, where the cultured stem cells are subsequently detached from the culture plate at a high cellular density to form a three-dimensional cell cluster and grown in the form of a three-dimensional cell cluster while differentiating into vascular cells.

In addition, the present invention provides a cell therapy composition for the treatment of vascular disease or wound healing having a three-dimensional cell cluster as an active ingredient, the three-dimensional cell cluster being composed of vascular cells differentiated from stem cells by the above method.

Further, the present invention provides a tissue engineering composite scaffold for regeneration of blood vessels in which a three-dimensional cell cluster composed of vascular cells differentiated from stem cells by the above method is loaded on a biodegradable scaffold.

The differentiation method according to the present invention utilizes the physical interactions between stem cells and the hydrophobic surface of a culture plate or biochemical interactions between stem cells and growth factors immobilized on the same culture plate surface to culture the stem cells in the form of a three-dimensional cell cluster. By doing so, hypoxia is created within the cell cluster, resulting in an overproduction of angiogenic stimulators. As a result, differentiation of the stem cells into vascular endothelial cells can be effectively induced. If the three-dimensional cell cluster obtained by the differentiation method of the present invention is transplanted into the body, mature blood vessels can be effectively formed in vivo by the actions of the abundant angiogenic stimulators and vascular cells differentiated from the stem cells. Accordingly, the cell cluster according to the present invention is useful as a cell therapy agent for the treatment of vascular diseases or wound healing. In addition, the cell cluster according to the present invention can be useful as a composite scaffold for regeneration of blood vessels in combination with a biodegradable scaffold.

DESCRIPTION OF THE EMBODIMENTS

Figure 1A:
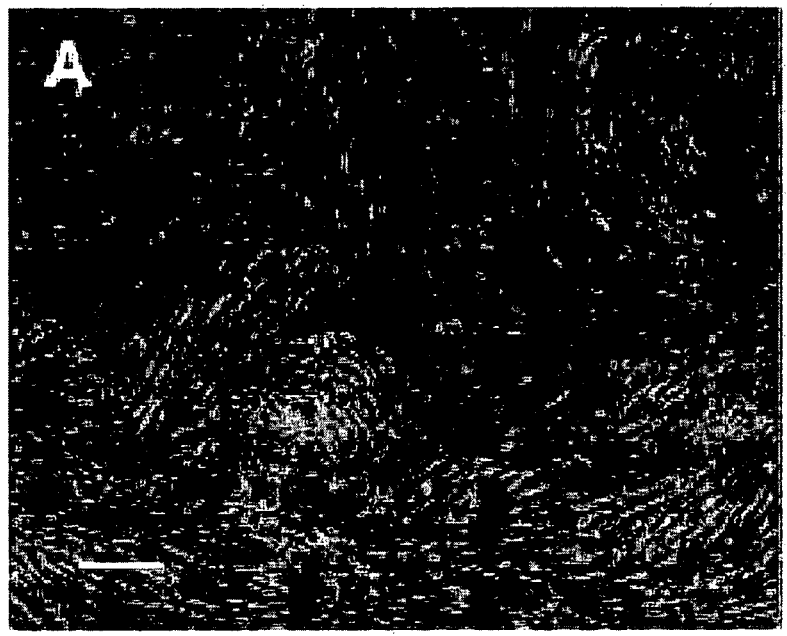
FIG. 1a is a photograph showing multipotent adipose stem cells isolated from human subcutaneous adipose tissue, observed using a contrast-phase microscope under a magnification of 40.

The present invention provides a method for the differentiation of stem cells into vascular cells by culturing stem cells in the form of a three dimensional cell cluster.

The present invention is based on the discovery that the adherent activity of stem cells varies depending on the surface characteristics of a culture plate and the morphology of the cells to be finally obtained may differ according to the extent of the adhesion. According to the above finding, if stem cells are cultured on a culture plate with a surface of hydrophobic property, there is not a sufficiently strong adherent activity between the stem cells and the culture plate due to the hydrophobic surface, and the stem cells, at the early stage, proliferate while being attached to the surface of the culture plate due to cell-matrix interactions. However, with the passage of culture time, the stem cells, at high cell density, are detached from the surface and grow while floating in a culture medium and form a three-dimensional cell cluster through cellular interactions. In such a three-dimensional cell cluster, differentiation of the stem cells into vascular cells occurs.

Cell adhesion onto a surface of biological materials occurs by various mechanisms and can be classified into specific cell adhesion mediated by biological recognition and non-specific adhesion governed by static electrical or surface energy. Specific cell adhesion occurs when specific peptide ligands present in ECM proteins (e.g., collagen, fibronectin, laminin, etc.), such as Arg-Gly-Asp (RGD), bind to integrins that are adhesion receptors present on the cell membrane. Non-specific cell adhesion is a process by which the surface to be adhered by cells is made electropositive to induce the adhesion of the cells since cell membranes mainly composed of phospholipids are electrically negative. Most currently available tissue cell culture plates have surfaces which are made electropositive by plasma treatment based on such non-specific cell adhesion principle. In addition to the method described above, cell adhesion can be induced if the surface to be adhered by cells is imparted with surface energy corresponding to that of the cell membrane.

Adhesion-dependent cells such as epithelial cells or mesenchymal cells, which adhere to the extracellular matrix and grow, unlike blood cells, go into apoptosis, if they do not adhere to the matrix. Such apoptosis is called anokis. The adhesion of cells to the matrix greatly affects the growth and differentiation of the cells.

The in vitro cell culture of such adhesion-dependent cells involves intercellular interactions and cell-matrix interactions. Only when cell-matrix interactions are stronger than intercellular interactions can cells proliferate while forming a two-dimensional monolayer on the surface of a culture plate. Meanwhile, at the early stage the cells cannot adhere to the surface of the culture plate because the intercellular interactions are stronger than the cell-matrix interactions, most cells are unable to proliferate, leading to death. Accordingly, in order to induce a three-dimensional culture of adhesion-dependent cells, it is important that at the early stage, the cells are cultured while being attached to the surface of a culture plate and subsequently, where intercellular adhesion is induced at a high cell density, an environment where the cells can be detached from the culture plate and grow while floating and form a three-dimensional cell cluster needs to be created.

Therefore, the present inventors invented a method of appropriately controlling the force involving cell-matrix interactions rather than that involving cellular interactions, in order to induce cell culture in the form of a three-dimensional cell cluster. More specifically, the present inventors developed a method of gently inducing cell adhesion such that at the early stage of culture, the cells proliferate while being individually adhered onto the surface of a culture plate but after passage of time, adhesion between cells is induced at a high cellular density, and the cells are detached from the surface.

In order to achieve the above, in the present invention, culture plates having various surface characteristics were screened for cell adherent activity of stem cells using adipose stem cells. As a result, in the culture plates coated with ECM proteins such as collagen, fibronectin, and laminin, and those imparted with an electropositive property by plasma treatment on the surfaces, cell-matrix interactions were superior and thus the adipose stem cells proliferated while being adhered to the surface of the culture plates. On the other hand, the adhesion of the adipose stem cells was very weak in the culture plates adsorbed with bovine serum protein (BSA) used to impart hydrophilic properties and with a synthetic saccharide polymer having an amphipathic property, i.e., poly-(N-p-vinylbenzyl-4-O-a-D-glucopyranosyl-D-gluconamide (PVMA), poly-(N-p-vinylbenzyl-4-O-b-D-galactopyranosyl-D-gluconamide (PVLA), and poly-(N-p-vinylbenzyl-1,2-D-glucuronamide (PV6Gna). However, it was surprisingly found that in culture plates having a polystyrene surface with a hydrophobic property, cell-matrix interactions were not sufficiently strong and thus at the early stage, the adipose stem cells adhered and grew onto the surface of the culture plate, but after passage of a certain period of time, they were detached from the surface and grown while floating in a culture medium.

Accordingly, the present inventors discovered that if stem cells are cultured in the form of a three-dimensional cell cluster by adjusting the culture time-dependent adherent activity of stem cells by using a culture plate with a surface having a hydrophobic property, the stem cells can be differentiated into vascular cells.

Based on the above finding, the differentiation method according to the present invention comprises culturing stem cells by adhering them onto a culture plate with a surface having a hydrophobic property (step 1), where the cultured stem cells are later detached from the culture plate as their density increases to form a three-dimensional cell cluster while growing in a floating state in the culture medium (step 2) and differentiate into vascular cells while growing in the form of the three-dimensional cell cluster (step 3).

Step 1 involves culturing stem cells by attaching the stem cells onto a culture plate with a surface having a hydrophobic property. In this step, the stem cells are attached onto a culture plate via a physical interaction with the hydrophobic surface or via a biochemical interaction with a growth factor having adhesion activity to the stem cells that has been immobilized on the surface of the culture plate.

Stem cells which can be used in step 1 include cells that remain undifferentiated while retaining the capability of being differentiated into all types of cells constructing the body, such as blood vessels, neurons, blood, cartilage, etc., in particular, multipotent adult stem cells that are activated only in tissues having the same characteristics as their original tissue. Examples of such stem cells may include adipose stem cells, mesenchymal stem cells, bone marrow stem cells, umbilical cord blood stem cells, neural stem cells, induced pluripotent stem cells, etc.

In one embodiment of the present invention, multipotent stem cells derived from human adipose tissues derived are used. The multipotent stem cells are cultured by physically attaching the stem cells to a culture plate having a surface of a hydrophobicity property via cell-matrix interaction. Human adipose tissues suitable for the present invention are those composed of mature adipose cells and connective tissues surrounding the same and can be easily obtained from patients themselves or others having the same phenotype. Irrespective of where they are located in the body, any adipose tissue obtained by any method for collecting fat can be used. Representative adipose tissues include subcutaneous adipose tissue, bone marrow adipose tissue, mesentery adipose tissue, stomach adipose tissue, retroperitoneal adipose tissue, etc.

Adipose stem cells can be isolated from human adipose tissues by using known methods. For example, as disclosed in PCT International Patent Publication Nos. WO 2000/53795 and WO 2005/04273, the adipose stem cells can be obtained by liposuction, precipitation, enzymatic treatment with collagenase, removal of drifting cells such as erythrocytes using a centrifuge, etc.

In some embodiments of the present invention, human adipose tissue obtained as incidentals during liposuction are washed with a phosphate buffered saline (PBS) and then chopped. The chopped tissues are treated at 37° C. for a time period of 1 to 6 hours using a serum-free medium in which collagenase type I is added. Subsequently, after the PBS wash, the supernatant is removed by centrifugal separation at a speed of 1000 rpm while the pellet is separated from the bottom. The separated pellet is washed with PBS and then subjected to centrifugation at a speed of 1000 rpm for 5 minutes. The above obtained supernatant is filtered while removing drifting cells such as erythrocytes and cell debris, and then washed with PBS. The supernatant is cultured in a medium with serum for 24 hours and then the cells that have not been attached to the bottom of the culture plate are washed with PBS, where the serum-containing medium is replaced every two (2) days, and cultured to obtain multipotent adipose stem cells. The adipose stem cells isolated as above show a superior proliferation rate despite numerous passages, i.e., until the passage number reaches sixteen (16). Accordingly, as for the multipotent adipose stem cells isolated from human adipose tissues according to the present invention, the primary culture may be used as is or the cells that have undergone at least ten subcultures under 60% confluency may be used in the subsequent step of forming a three-dimensional cell cluster. If adipose stem cells that have been sufficiently proliferated by subculture are used, then differentiation into vascular endothelial cells can be induced in a high yield in a short period of time.

When the adipose stem cells thus prepared are inoculated and cultured on a culture plate having a surface with a hydrophobic property, due to the hydrophobic surface, cell-matrix interactions occur between the adipose stem cells and the culture plate and the adipose stem cells proliferate while being attached to the surface of the culture plate via physical adsorption.

Culture plates with a surface having a hydrophobic property suitable for the present invention are conventional cell culture plates having a surface which is treated with polymers that impart a hydrophobic property to the cell culture plates or cell culture plates made from such polymers. Such polymers may be, but not limited to, one selected from polystyrene, polymethylmethacrylate (PMMA), polyethylene terephthalate (PET), polyvinylchloride (PVC), polyethylene (PE), polypropylene (PP), polytetrafluoroethylene (PTFE), aliphatic polyester based polymer selected from poly(L-lactic acid) (PLLA), poly(D,L-lactic acid) (PDLLA), poly(glycolic acid) (PGA), poly(caprolactone) (PCL), poly(hydroxyalkanoate), and polydioxanone (PDS), polytrimethylencarbonate, copolymers thereof such as poly(lactic acid-co-glycolic acid) (PLGA), poly(L-lactic acid-co-caprolactone) (PLCL), poly(glycolic acid-co-caprolactone) (PGCL), derivatives thereof, etc. In addition, culture plates suitable for the present invention may have a silanized surface, carbon nano tube surface, hydrocarbon coated surface and metallic (e.g., stainless steel, titanium, gold, platinum, etc.) surface as the surface with a hydrophobic property.

In another embodiment of the present invention, in order to adhere stem cells onto a culture plate more effectively than physical adsorption by interactions between the stem cells and the hydrophobic culture plate, biochemical interactions between the stem cells and growth factors having adherent activity to the stem cells that are immobilized onto the surface of the culture plate may be used.

As growth factors suitable for the present invention, any growth factor having an adherent activity to stem cells can be used, for example vascular endothelial growth factor (VEGF), fibroblast growth factor (FGF), epidermal growth factor (EGF), platelet-derived endothelial growth factor (PDFG), hepatocyte growth factor (HGF), insulin-like growth factor (IGF) and heparin binding domain (HBD). These growth factors can be immobilized on the surface of a culture plate at a concentration between 5 and 100 µg/ml. In some embodiments of the invention, FGF as a growth factor having adherent activity to stem cells is immobilized on the hydrophobic surface of a culture plate. FGF (NCBI GenBank Accession No. EF506888.1) is a growth factor which binds to a FGF receptor or HSPG present on the membrane of stem cells to exhibit biological functions important for differentiation or proliferation when culturing adipose stem cells, mesenchymal stem cells, embryonic stem cells, etc.

Immobilization of a growth factor on the surface of a culture plate uses the same method as immobilization of a polypeptide on a solid substrate surface, which can be achieved by any known method in the art. Conventionally, physical adsorption, covalent binding via non-selective chemical reactions, etc., can be used. In such immobilization methods, the following known methods may be used: a method of immobilizing proteins by means of biotin-streptavidin/avidin interaction by biotinylating the proteins and applying the biotinylated proteins onto a solid surface treated with streptavidin or avidin; a method of immobilizing proteins by integrating active moieties (chemical functional groups for immobilizing proteins by chemical binding) on a substrate using plasma; a method of immobilizing proteins on a solid substrate surface, on which a porous sol-gel thin film having a sufficiently increased specific surface area is formed via a sol-gel method, by physical adsorption to the porous sol-gel thin film; a method of immobilizing anti-thrombotic proteins on polytetrafluoroethylene (PTFE) surfaces by using a plasma reaction; a method of immobilizing proteins by binding enzymes in which at least two cationic amino residues are successively fused to two enzymes; a method of immobilizing proteins on a hydrophobic polymer layer bound to a solid phase support using a matrix; a method of immobilizing proteins on a plastic surface using a buffering component; and a method of immobilizing proteins by contacting said proteins with a solid surface having a hydrophobic property in an alcohol solution.

In one embodiment of the present invention, a polypeptide linker that is capable of being expressed in a large amount and is easy to purify is used. The immobilization is carried out in the form of a recombinant protein having a polypeptide linker and a growth factor in which the amino terminal group of the growth factor is fused to the carboxyl terminal group of the polypeptide linker. In the present invention, a growth factor essential for the differentiation and proliferation of stem cells is immobilized on the hydrophobic surface in the form of a recombinant protein with a polypeptide linker while retaining the original biological activity of the growth factor. The immobilized growth factor's adhesion activity to stem cells enables the stem cells to be adhered onto the surface and promotes effective culture of the stem cells.

As a polypeptide linker suitable for the invention, any linker may be used as long as its carboxyl terminal group can be linked to an amino terminal group of a growth factor and its amino terminal hydrophobic domain allows for adhesion onto a culture plate with a hydrophobic surface. Any linker that can be mass produced and easily purified in the form of a recombinant protein without affecting the stem cell culture may be used. Such polypeptide linkers may be maltose-binding protein (MBP), hydrophobin, hydrophobic cell penetrating peptides (CPPs), etc.

In some embodiment of the invention, a growth factor is immobilized onto a surface of a culture plate using maltose-binding protein (MBP) as a polypeptide linker. MBP (NCBI GenBank Accession No. AAB59056), which is located in the periplasm across the cell membrane of *Escherichia coli*, is a periplasm protein involved in the migration of saccharides such as maltose or maltodextrin.

MBP, which is mainly used for the production of useful exogeneous proteins into recombinant proteins, is produced from malE gene in the cell. When genes encoding an exogeneous protein are inserted into downstream of the cloned malE gene and expressed in the cell, a recombinant protein in which two proteins are combined can be easily produced in high yields. In particular, where exogeneous proteins to be expressed are small or less stable in other host cells, it is advantageous to express them in a recombinant protein form using MBP as above. The exogeneous proteins expressed from malE-fused genes can be isolated using MBP's binding affinity to maltose. For example, a resin coated with amylase, which is a poly-maltose, is reacted with a cell homogenate. The reacted resin is washed several times to remove other contaminated proteins and then a high concentration of maltose is added to the resin to compete, where only the desired protein can be eluted.

Therefore, the present invention provides a recombinant protein using a MBP that is expressed in *E. coli*. and is easy to express and purify due to its superior binding ability to maltose, in which a carboxyl terminal group of maltose is linked to an amino terminal group of FGF. This recombinant protein is immobilized onto a culture plate with a surface having a hydrophobic property by simple physical adsorption using a hydrophobic domain of MBP as a linker. Subsequently, stem cells are attached to the surface of the culture plate through adhesion between the FGF portion which still maintains the biological activity in the immobilized recombinant protein and the stem cells. While the carboxyl terminal group in MBP is used in binding to FGF for preparing the recombinant protein, the amino terminal group containing a hydrophobic domain is used in physical adsorption to the hydrophobic surface in the subsequent steps.

The MBP-FGF recombinant protein retaining the adherent activity to stem cells provided as above where the carboxyl terminal group of the maltose binding protein (MBP) is fused to the amino terminal group of the fibroblast growth factor (FGF) may have an amino acid sequence of SEQ ID NO: 1.

The MBP-FGF recombinant protein can be prepared using conventional chemical synthesis or genetic recombination technology, or obtained by recovering the recombinant protein after culturing transformed bacteria expressing the recombinant protein under suitable conditions. Such transformed bacteria include *E. coli*. transformant K12 TB1 (pMAL-bFGF) which was deposited in the Gene Bank in Korea Research Institute of Bioscience & Biotechnology under Deposit No. KCTC-11505BP on Apr. 28, 2009.

The MBP-FGF recombinant protein thus obtained is immobilized onto a culture plate having a hydrophobic surface without requiring any special treatment. That is, the recombinant protein is spontaneously immobilized via physical adsorption of the hydrophobic domain positioned in the amino terminal group of a polypeptide linker of the same recombinant protein to the hydrophobic surface.

In some embodiments of the present invention, the MBP-FGF recombinant protein is diluted to 1 ng/ml to 0.5 mg/ml in a suitable buffer, e.g., phosphate buffered saline (PBS), Twin 20/PBS, Tris-HCl buffer, bicarbonate buffer, etc. The diluted solution is added to a culture plate with a hydrophobic surface and reacted at 4-25° C. for 1-24 hours and then the recombinant protein is immobilized onto the hydrophobic surface via physical adsorption of a hydrophobic domain located in the amino terminal group of MBP to the hydrophobic surface. The MBP-FGF recombinant protein to be immobilized on the hydrophobic surface may have a concentration of from 5 to 100 µg/ml.

In the recombinant protein immobilized onto a hydrophobic surface of a culture plate as above, because FGF which is important for cell recognition is exposed on the outside, it can easily bind to FGF receptors or HSPG present on the membrane of stem cells and thus play a key role in regulating cellular functions. Accordingly, if stem cells are cultured on a FGF-immobilized culture plate, they can then be cultured while being attached onto the culture plate via direct interactions between the stem cells and FGF.

As described above, if in step 1, stem cells are cultured by physically attaching them to a culture plate having a surface with a hydrophobic property via cell-matrix interactions or they are cultured while being bonded to a growth factor immobilized on a surface of the culture plate via biochemical interactions with the growth factor, the stem cells proliferate while being attached to the surface of the culture plate at an early stage.

In step 2, the stem cells that proliferate while being attached to the surface of the culture plate in step 1 are detached from the surface of the culture plate at a high cell density where intercellular interactions are stronger than cell-matrix interactions. The detached stem cells grow while floating in a culture medium and aggregate to one another to form a floating three-dimensional cell cluster of a millimeter size that is visibly detectable.

In certain embodiments, a non tissue culture plate (NTCP) made of polystyrene is used as a culture plate having a surface with a hydrophobic property and inducing relatively weak cell adhesion to the plate surface. In the culture plate, human adipose stem cells are inoculated to induce formation of a three-dimensional cell cluster. In the early stage, the adipose stem cells inoculated to the polystyrene NTCP proliferate in a second-dimensional monolayer while being adhered to the surface of the culture plate due to the weak cell adhesion induced by cell-matrix interactions. As the density of the cells increases according to the passage of culture time, intercellular interactions become stronger than cell-matrix interactions and the cells cultured in a second-dimensional monolayer are detached from the surface of the culture plate. In this regard, it is important to culture the adipose stem cells while they are attached to the surface of the culture plate in the early stage. If the stem cells are cultured in a floating state without being attached to the surface in the early stage, the size of the formed three-dimensional cell cluster is small and most of the cells perish. If the cells detached from the culture plate are further cultured in a floating state in a culture medium, they aggregate to one another via intercellular interactions to form a three-dimensional cell cluster. In the three-dimensional cell cluster thus formed, cells are weakly combined to each other in the early stage. With the passing of culture time, the adhesion between cells is strengthened by intercellular interactions to form a compact three-dimensional cell cluster.

The three-dimensional cell cluster formed according to the present invention has a visually detectable size, specifically having a diameter of from 400 µm to 1 mm. In the present invention, the size of the three-dimensional cell cluster is very important for the differentiation of stem cells into vascular endothelial cells. This is because the larger the cell cluster is, the smaller the amount of oxygen transmitted into the cell cluster. This creates hypoxia inside the cell cluster by which the production of various angiogenic stimulators affecting the differentiation of vascular endothelial cells is induced. Accordingly, when the diameter of a three-dimensional cell cluster is less than 400 µm, stem cells may not be effectively differentiated into vascular endothelial cells. On the other hand, when the diameter is greater than 1 mm, apoptosis may be induced due to excessive oxygen deficiency inside the cell cluster.

In general, if hypoxia is created by artificially restricting the oxygen supply to monolayer-cultured cells, angiogenic stimulators such as VEGF may be produced. However, since the angiogenic stimulators thus formed are likely to be diffused into the excessive amount of medium, the chance that the cells will actually absorb the angiogenic stimulators is slim. On the other hand, if a cell cluster is formed as in the present invention, the angiogenic stimulators produced inside the cell cluster can directly act on the cells. Accordingly, the stem cells can grow in the presence of a high concentration of angiogenic stimulators, and thus, can be effectively differentiated into vascular endothelial cells.

In order to form a three dimensional cell cluster having a size of the above mentioned range, it is desirable that in step 2, stem cells are inoculated at a concentration of from $1 \times 10^4$ to $3 \times 10^5$ cells/cm$^2$. In the case where the concentration of the inoculated stem cells is less than $1 \times 10^4$ cells/cm$^2$, the size of the cell cluster cannot be reproduced, while when the concentration is greater than $3 \times 10^5$ cells/cm$^2$, apoptosis may occur due to inoculation of an excessive number of cells.

In some embodiments of the present invention, in order to induce the formation of a three-dimensional cell cluster of adipose stem cells, the isolated adipose stem cells are suspended in a serum medium and then inoculated to each well of polystyrene well plates at a concentration of from $1 \times 10^4$ to $3 \times 10^5$ cells/cm$^2$. As a result, three days after culturing at a concentration of at least $2 \times 10^4$ cells/cm$^2$, it is confirmed that a three-dimensional cell cluster having a diameter in the range of from 500 µm to 1 mm is induced. The size of the formed three-dimensional cell cluster varies depending on the initial concentration of the inoculated adipose stem cells. Specifically, inoculation of adipose stem cells at a concentration of at least $4 \times 10^4$ cell/cm$^2$ is convenient to form and recover a visibly detectable size of a three-dimensional cell cluster.

In Step 3, stem cells grow in the form of the three-dimensional cell cluster formed in Step 2 while being differentiated into vascular endothelial cells. If the stem cells are cultured in the form of a three-dimensional cell cluster, oxygen transmission to the inside of the cell cluster decreases, thereby creating hypoxia. The hypoxia created inside the cell cluster induces the production of various angiogenic stimulators affecting the vascular endothelial cell differentiation, finally leading to the differentiation of the stem cells into vascular endothelial cells.

In Step 1, in the case where the stem cells are cultured by attaching to a culture plate having a surface of a hydrophobic property, it is preferred to culture the stem cells inoculated to the culture plate at a temperature between 35° C. and 38.5° C. for 1 to 7 days so that a three-dimensional cell cluster composed of vascular endothelial cells differentiated from the stem cells can be obtained.

Alternatively, in Step 1, in the case where the stem cells are cultured by attaching them to a culture plate on which a growth factor having adherent activity to the stem cells is immobilized, it is desirable to culture the stem cells inoculated to the culture plate at a temperature between 35° C. and 38.5° C. for 1 to 7 days so that a three-dimensional cell cluster composed of vascular endothelial cells differentiated from the stem cells can be obtained.

As for a suitable medium for the above culture, any medium, with or without serum, conventionally used in the culture and/or differentiation of stem cells can be used without limitation, for example Dulbeco's modified eagle medium (DMEM), Ham's F12, and medium in which a serum is added to a mixture thereof. In certain embodiments of the invention, a medium in which a fetal bovine serum (FBS) is added to DMEM/F12 medium where DMEM and Ham's F12 are mixed in a volume ratio of 1:1 is used.

Since the three-dimensional cell cluster formed by culturing stem cells by attaching them to the surface of a culture plate as above has a visibly detectable size, specifically a diameter ranging from 400 µm to 1 mm, it can be easily recovered through filtration or centrifugation. The three-dimensional cell cluster thus recovered is degraded by enzymatic treatment using collagenase, trypsin or dispase, mechanical treatment using pressure, or a combined treatment of the foregoing and is used in unicellular forms or can be used in a three-dimensional cell cluster form as is.

The three-dimensional cell cluster formed according to the present invention may be analyzed using immunological staining. The three-dimensional cell cluster shows an immunological phenotype specific to the vascular endothelial cells, by which it can be confirmed that the adipose stem cells differentiated into vascular endothelial cells. Specifically, the three-dimensional cell cluster formed according to the present invention exhibited a positive reaction with respect to CD29, which is a surface antigen expressed on mesenchymal stem cells and epithelial cells, CD34, KDR (kinase insert domain receptor; vascular endothelial growth factor receptor 2), and CD31 (endothelial cell adhesion molecule, PECAM), which are surface antigens expressed on vascular endothelial cells, and smooth muscle actin (SMA) and myosin heavy chain (MHC) which is expressed in smooth muscles. On the other hand, the three-dimensional cell cluster formed according to the present invention exhibited a negative reaction with respect to osteocalcin, nestin, and MAP-2, which are surface antigens expressed in bone cells and neural cells.

Based on the above results, it can be confirmed that the stem cells are differentiated into vascular cells because the cells obtained by culturing stem cells in a three-dimensional cell cluster form according to the present invention are found to express surface antigens specific to vascular cells.

As described above, the method of differentiating stem cells into vascular endothelial cells according to the present invention can effectively differentiate stem cells into vascular endothelial cells by a three-dimensional cell cluster which is formed by adjusting the adherent activity of stem cells to a culture plate by using a culture plate having a surface with a hydrophobic property or a growth factor immobilized onto the culture plate surface. In addition, if the three-dimensional cell cluster obtained according to the present differentiation method is transplanted in vivo, mature blood vessels can be effectively formed in the body by abundant angiogenic stimulators and vascular cells differentiated from the stem cells. Accordingly, the cell cluster according to the present invention can be used not only as a cell therapy agent for vascular diseases or wound healing, but also as a composite scaffold for use in tissue engineering for the regeneration of blood vessels along with a biodegradable scaffold.

Therefore, the present invention provides a cell therapy composition useful for treating vascular diseases or would healing, the composition containing as an effective ingredient a cell cluster composed of the vascular cells differentiated from stem cells by the method described above.

The vascular diseases in the present invention include cardiovascular disease, cerebrovascular disease, and ischemia disease, such as, for example, atherosclerosis, stable and unstable angina pectoris, peripheral cardiovascular disease, hypertension, heart failure, peripheral circulatory disturbance, myocardial infarction, stroke, transient and ischemic attack, subarachnoid hemorrhage, etc.

The cell therapy composition according to the present invention can be administered in an amount of $1.0 \times 10^7$ to $1.0 \times 10^8$ cell/kg (body weight), more specifically $1.0 \times 10^5$ to $1.0 \times 10^8$ cell/kg (body weight), based on the vascular endothelial cells differentiated from stem cells which constitute the cell cluster as an active ingredient of the composition. However, the dosing amount can be prescribed depending on the formulation methods, administration methods, age, weight, sex, the severity of disease, food, administration time, administration route, excretion rate, and response sensitivity. A person skilled in the art could appropriately adjust the dosing amount in consideration of such factors. The composition can be administered once a day or at least twice a day to the extent that adverse effects are clinically acceptable. In addition, it can be administered to one site or two or more sites. Further, the composition can be administered to non-human animals at the same amount per kilogram. Otherwise, the composition can be administered in an amount obtained from converting the above dosing amount based on, for example, the volume ratio (e.g., mean value) of the ischemic organ (e.g., heart) of the subject animal and human. The subject animals to be treated by the present invention include humans and other mammals, specifically human, monkeys, rats, mice, rabbits, sheep, cows, dogs, horses, pigs, etc.

The cell therapy composition according to the present invention may comprise a cell cluster, as an active ingredient, and a pharmaceutically acceptable carrier and/or additives. For example, sterilized water, physiological saline, conventional buffers (phosphoric acid, citric acid, other organic acids, etc.), stabilizers, salts, anti-oxidants (ascorbic acid, etc.), surfactants, suspensions, isotonic agents, preservatives may be included. For topical administration, it may be desirable to combine the present composition with organic compounds such as biopolymers, and inorganic compounds such as hydroxyapatite, specifically collagen matrix, polylactic acid polymer or copolymer, polyethyleneglycol polymer or copolymer and chemical derivatives thereof, etc. In the case where the cell therapy composition according to the present invention is formulated into a dosage form suitable for injection, it is desirable that a cell cluster is dissolved in a pharmaceutically acceptable carrier or frozen as a solution.

The cell therapy composition according to the present invention can appropriately include suspensions, dissolution aids, stabilizers, isotonic agents, preservatives, anti-adhesion agents, surfactants, diluents, excipients, pH adjusting agents, pain relieving agents, buffers, sulphur-containing reducing agents, anti-oxidants, etc., depending on its administration method or dosage form as necessary. Pharmaceutically acceptable carriers and preparations suitable for the present invention including those mentioned above are described in detail in Remington's Pharmaceutical Sciences, 19$^{th}$ ed., 1995.

The cell therapy composition according to the present invention can be formulated by using pharmaceutically acceptable carriers and/or excipients according to methods which can be easily carried out by those skilled in the art so that the composition can be manufactured as a unit dosage form or incorporated into a multiple dose container. The dosage forms may be a solution, suspension, or emulsion in oil or aqueous medium, or powders, granules, tablets, or capsules.

The cell therapy composition of the present invention comprising the cell cluster composed of the vascular cells differentiated from stem cells as described above is very useful for treating wounds, cardiovascular diseases, cerebrovascular diseases, ischemic diseases, etc.

The present invention also provides a composite scaffold for use in tissue engineering for blood vessel regeneration containing the cell cluster composed of the vascular cells differentiated from stem cells as an active ingredient.

The tissue engineering composite scaffold according to the present invention is characterized in that the cell cluster composed of the vascular cells differentiated from stem cells is loaded in a scaffold made by molding a biodegradable polymer.

The biodegradable polymer, which spontaneously and slowly decomposes in the body after a certain period of time, refers to a polymer possessing at least one characteristic from biocompatibility, blood-compatibility, anti-calc sintering property, and the capability of forming nutritional components and intercellular matrix. Such biodegradable polymers include, but are not limited to, fibrin, collagen, gelatin, chitosan, alginate, hyaluronic acid, dextran, polylactic acid, poly(glycolic acid (PGA), poly(lactic acid-co-glycolic acid), poly(lactic acid-co-glycolic acid (PLGA), poly-ε-(caprolactone), polyanhydride, polyorthoester, polyvinylalcohol, polyethyleneglycol, polyurethane, polyacrylic acid, poly-N-isopropylacrylamide, poly(ethyleneoxide)-poly(propyleneoxide)-poly(ethyleneoxide) copolymers, copolymers, and mixtures thereof.

In the tissue engineering composite scaffold, a biodegradable polymer may be specifically present in an amount from 5 to 99% by weight. If the amount of the biodegradable polymer is less than the above range, the composite scaffold does not form well, resulting in a scaffold with lower mechanical strength. On the other hand, if the amount of the biodegradable polymer is greater than the above range, it is difficult to load the cell cluster.

The composite scaffold can be manufactured by molding a biodegradable polymer using known methods, for example solvent-casting and particle-leaching technique, gas forming technique, fiber extrusion and fabric forming process, thermally induced phase separation technique, emulsion freeze drying method, high pressure gas expansion, etc.

The composite scaffold manufactured as described above plays a role in transferring the loaded cell cluster into transplanted tissues, enabling the cells to be attached to the composite scaffold and grow in a three-dimensional manner and the new tissue to be formed. In order for the cells to be adhered to the composite scaffold and grow, the size and structure of the void of the scaffold matter. In order for a nutrition solution to evenly permeate into the interior of the scaffold so that the cells can grow well, it is desirable that the scaffold has interconnecting void structures. In addition, it is desirable that the composite scaffold according to the present invention has voids with an average diameter of 50-600 μm.

In the tissue engineering composite scaffold according to the present invention, it is desirable that the vascular endothelial cells are loaded in the composite scaffold at a concentration of $2 \times 10^4$ to $3 \times 10^5$ cell/cm$^2$ based on the vascular endothelial cells differentiated from stem cells which constitute a cell cluster as an active ingredient of the composite scaffold. If the concentration of the vascular endothelial cells is less than the above range, the effect of stimulating the vascular generation of vascular endothelial cells may be minimal. On the other hand, if the concentration is greater than the above range, there may be problems where the inoculated cells may perish due to nutrient and oxygen deficiencies.

The cell cluster inoculated in a composite scaffold as described above enables the vascular endothelial cells comprising the cell cluster to be differentiated into vascular cells, thereby effectively inducing the regeneration of vascular tissues in the organism into which the tissue engineering composite scaffold according to the present invention is transplanted.

Hereinafter, the present invention will be described in more detail with reference to the examples. However, it will be apparent to those skilled in the art that the following examples are for illustrative purposes only and that the invention is not intended to be limited by these examples.

EXAMPLES

Reference Example 1: Isolation of Multipotent Stem Cells from Human Adipose Tissue Subcutaneous adipose tissues of a normal person were supplied from the plastic surgery laboratory of Catholic University. The sample tissues were washed with a PBS solution containing 2% penicillin/streptomycin three times and contaminated blood was removed. Thereafter, the blood-removed tissues were chopped using surgical scissors. These chopped tissues were added in a tissue lysing solution (serum free DMEM+1% BSA (w/v)+0.3% collagenase type 1) which was prepared in advance and the solution was stirred at 37° C. for 2 hours, followed by centrifugation at a speed of 1,000 rpm for 5 minutes to separate the supernatant and pellets. The supernatant was discarded and the pellets remaining at the bottom were harvested. The harvested pellets were washed with PBS and then centrifuged at a rate of 1,000 rpm for 5 minutes to collect the supernatant. The collected supernatant was filtered with a 100 μm mesh to remove the tissue debris and was then washed with PBS. The thus isolated cells were cultured in a DMEM/F12 medium (Welgene) containing 10% FBS. After culturing for 24 hours, the non-adherent cells were washed with PBS and removed. The isolated cells were cultured while replacing the DMEM/F12 medium containing 10% FBS every two (2) days, and then human subcutaneous adipose tissue derived stem cells were obtained.

Figure 1B:
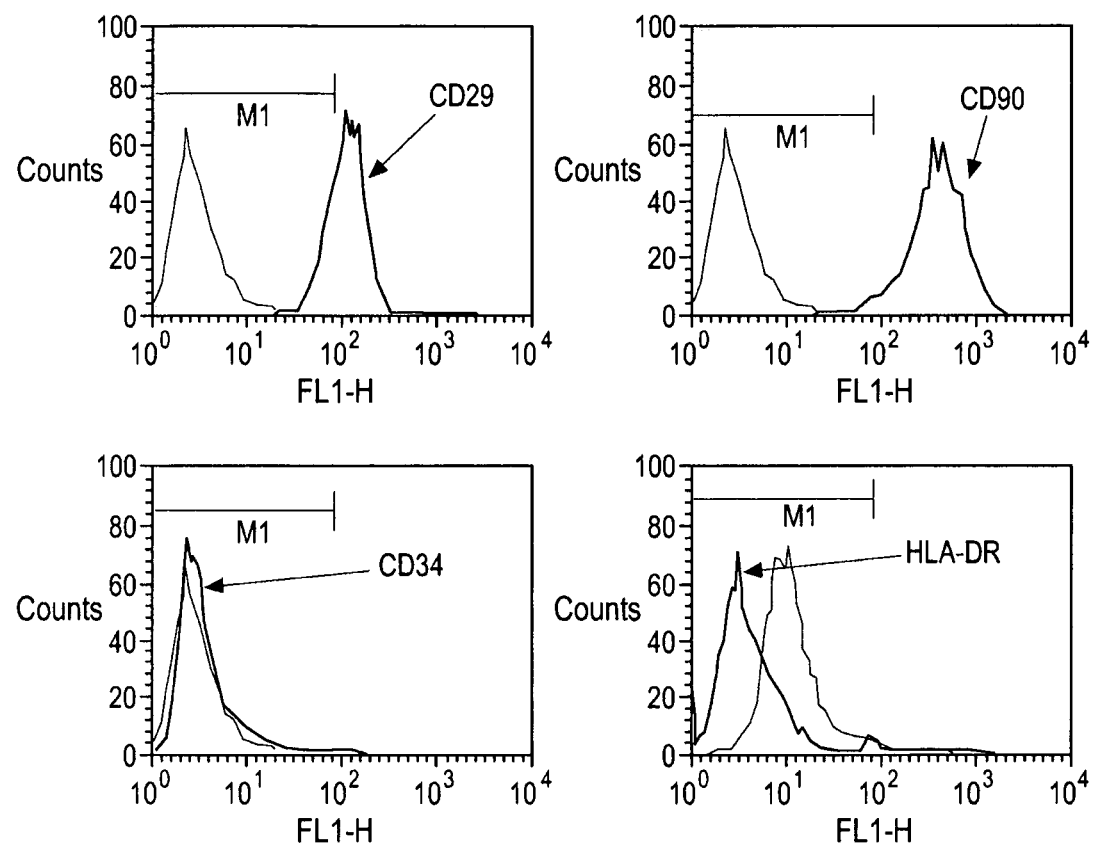
FIG. 1b shows the results of analyzing the expression profiles of surface antigens to multipotent adipose stem cells differentiated from human subcutaneous adipose tissues using flow cytometry.

FIG. 1a is a photograph showing multipotent stem cells isolated from human subcutaneous adipose tissue observed using a contrast-phase microscope (Nikon) under a magnification of 100. FIG. 1b shows the results from a flow cytometry analysis of the cell surface antigen expression profiles of the above multipotent stem cells. As surface antigens for confirming the presence of mesenchymal cells, CD29, CD90, and CD105 were used. The separation of stem cells and incorporation of other cells during culture were examined using CD34 and HLA-DR as surface antigens. Based on the above results, it was confirmed that the cells separated from human subcutaneous adipose tissue were adipose stem cells having a phenotype of mesenchymal stem cells.

Example 1: Adherent Activities of Adipose Stem Cells with Respect to Various Culture Plate Surfaces 20 μg/ml of various extracellular matrix proteins (i.e., collagen type 1, collagen type 4, fibronectin (FN), and laminine) and 100 μg/ml of saccharide polymer (i.e., poly-(N-p-vinylbenzyl-4-O-a-D-glucopyranosyl)-D-gluconamide), and 100 μg/ml of BSA were added in a 96-well plate for non-tissue cell culture (Non-Tissue Culture Treated 96-well Plate, "NTCP" made of polystyrene materials and having a surface with a hydrophobic property; Falcon). The well plate was stored at 25° C. for 4 hours so as to be coated, and then washed with PBS three times. 100 μg/ml BSA was added to the well plate to carry out blocking at 25° C. for 1 hour, followed by re-washing with PBS.

The adipose stem cells prepared in Reference Example 1 were suspended in a DMEM/F12 medium containing 10% FBS. The suspension was inoculated onto NTCP, a 96-well plate for tissue cell culture (Tissue Culture Treated 96-well Plate, "TCP," Falcon), and a well plate that is a NTCP coated with ECM proteins, saccharide polymers, and BSA at a concentration of $1.3 \times 10^4$ cell/cm$^2$ per well and the inoculated well plates were cultured in an incubator at 37° C. The degree of cell adhesion to the plates and their adhesion morphologies were observed at 0.25, 0.5, 1, 2, and 4 hours after inoculation. Subsequently, the cells adhered to the surface of the plates at each time point were dissolved in a cell lysis buffer and then quantified using a bicinchoninic acid (BCA) protein assay.

Figure 2:
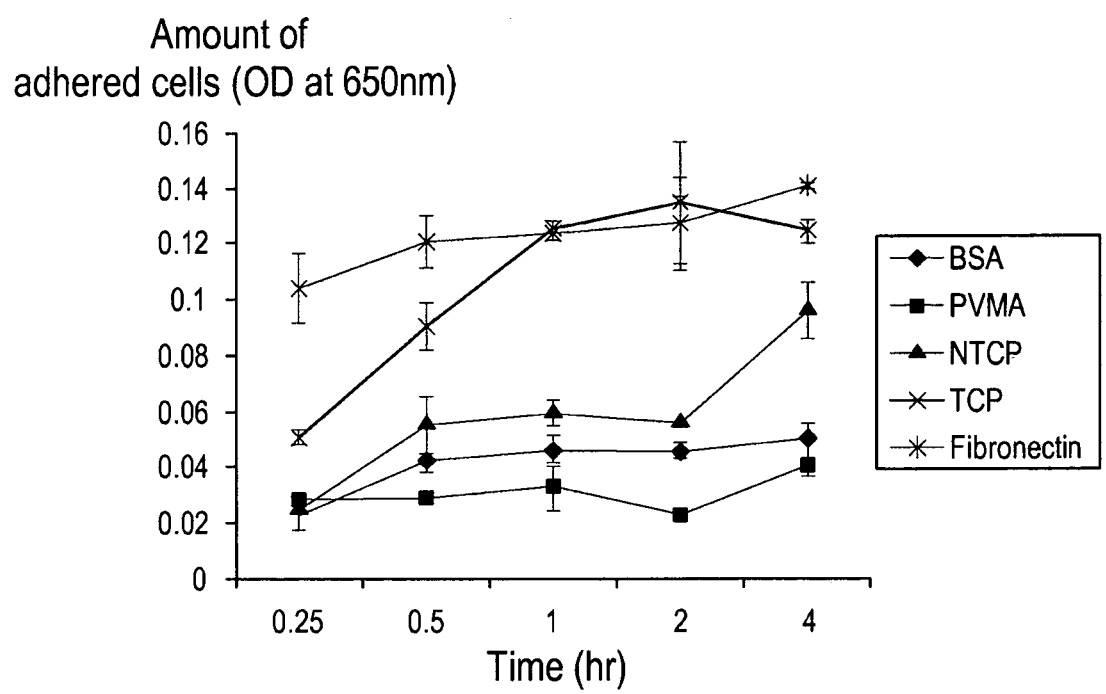
FIG. 2 is a graph showing the quantification of the adhesion activity of cells to various surfaces of culture plates by measuring the amounts of proteins adhered to the culture plate surfaces.

As a result, as shown in FIG. 2, no cell adhesion was observed in BSA- and saccharide polymer-coated NTCPs, irrespective of the culture time. However, in TCP- and fibronectin-coated NTCP, high cell adhesion rates were exhibited starting from one hour after cell inoculation. In NTCP, the cell adhesion rate was not high two hours after cell inoculation, but at four hours after cell inoculation, a rapid increase in the cell adhesion rate was observed. Based on the above, it was confirmed that in the plates coated with BSA and saccharide polymers, adipose stem cells had the lowest adherent activity while in TCP and plates coated with ECM proteins such as fibronectin, they had the highest adherent activity. In NTCP having a surface with a hydrophobic property, such as polystyrene, it was confirmed that the adherent activity of adipose stem cells was weakly induced.

Example 2: Formation of a Three-Dimensional Cell Cluster of Adipose Stem Cells

In order to examine the correlation between the adherent activity of adipose stem cells with respect to culture plate surface and the formation of a three-dimensional cell cluster, as in Example 1 above, adipose stem cells were inoculated on a 96-well plate for non-tissue cell culture (NTCP, polystyrene), NTCPs coated with ECM proteins (i.e., collagen and fibronectin), saccharide polymer (PVMA), and BSA, respectively, and a 96-well plate for tissue cell culture (TCP) at a concentration of $4\times10^4$ cell/cm$^2$ per well, followed by culturing in a DMEM/F12 medium containing 10% FBS for three (3) days. After the three day culture, whether or not a three-dimensional cell cluster of the adipose stem cells was formed on the surface of each culture plate was observed.

Figure 3:
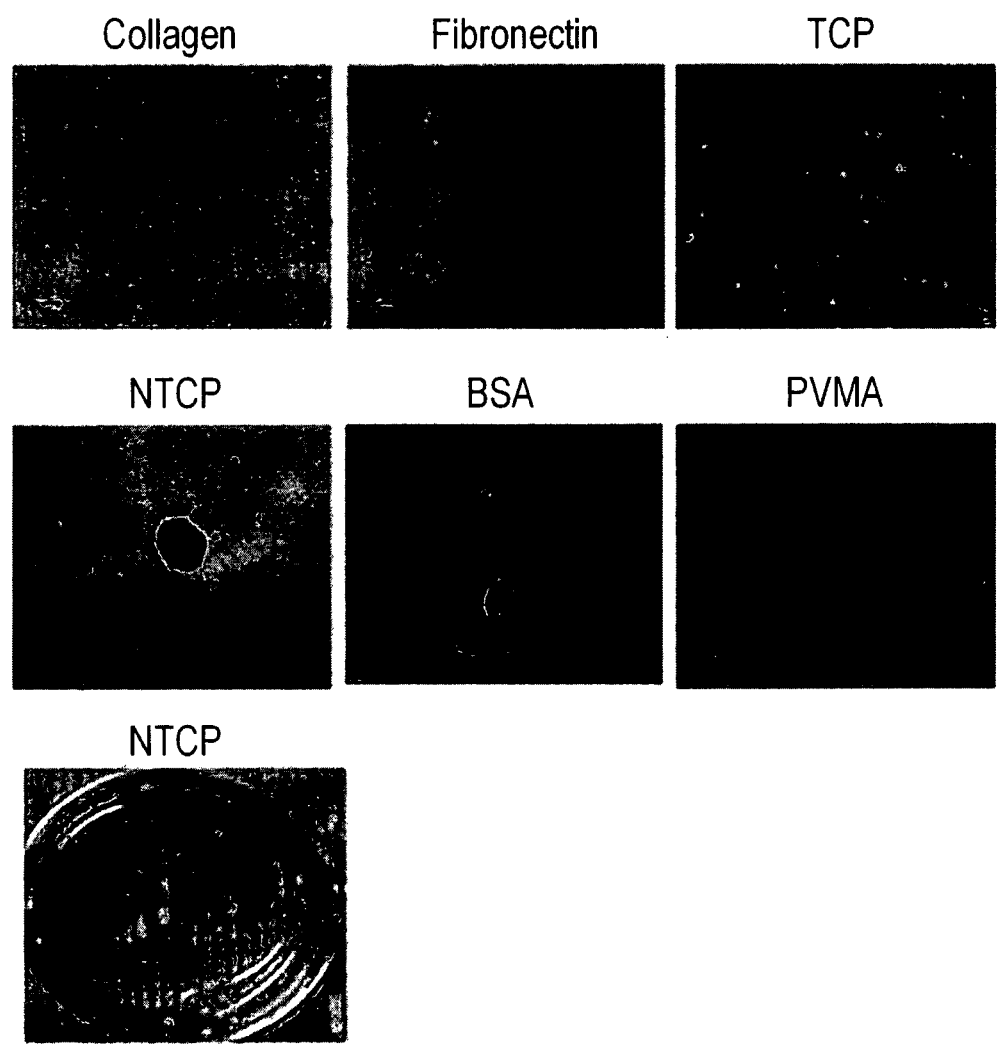
FIG. 3 is a photograph showing the formation of a three-dimensional cell cluster formed by culturing adipose stem cells in culture plates with various adherent activity to the cells, observed using a contrast-phase microscope under a magnification of 40.

As shown in FIG. 3, in NTCP where cell adhesion was weakly induced due to the hydrophobic surface, a visibly detectable size of a three-dimensional cell cluster was observed. The three-dimensional cell cluster had a diameter of at least about 500 µm. On the other hand, in fibronectin-coated NTCP or TCP where cell adhesion was strongly induced, the adipose stem cells were cultured in a monolayer while being adhered to the surface of the plates in a planar manner and thus no cell cluster was formed. In NTCP coated with BSA and PVMA in which cell adhesion hardly occurs, cell clusters with sizes not greater than 100 µm were sporadically formed but their size was too small. Based on the above results, it was confirmed that the formation of a three-dimensional cell cluster of adipose stem cells is influenced by the adherent activity of the stem cells with respect to the surface of the culture plates used. It was further confirmed that in order to form a three-dimensional cell cluster having a visibly detectable size, it is desirable to use a culture plate having a surface with a hydrophobic property such as NTCP made of polystyrene materials in which at an early stage, cell adhesion is less induced but as the density of cells increase according to the passage of time, the cells are detached from the plate and grow while floating.

In order to investigate the effective concentration required for forming a three-dimensional cell cluster that is visibly detectable in NTCP, the adipose stem cells obtained in Reference Example 1 were inoculated on 24-well and 6-well NTCPs which both contain a DMEM/F12 medium containing 10% FBS at a concentration of $0.5\times10^4$ to $1\times10^5$ cells/cm$^2$, followed by culturing the same for three (3) days. As a result, it was confirmed that the formation of a three-dimensional cell cluster having a visibly detectable size is efficiently induced at a concentration of at least $2\times10^4$ cells/cm$^2$.

Example 3: Immunological Analysis of the Three-Dimensional Cell Clusters

As in Example 2 above, adipose stem cells were inoculated in a 6-well NTCP at a concentration of $4\times10^4$ cells/cm$^2$ and cultured to form a three-dimensional cell cluster. The three-dimensional cell cluster was harvested and fixed at −70° C. using an OCT compound and then cut to a thickness of 4 µm using a microtome. The fragment was fixed on a glass slide and immunologically stained. Alternatively, the harvested three-dimensional cell cluster was physically broken up using a syringe, and then placed and adhered to a glass slide for 4 hours. Subsequently, the glass slide was washed with PBS several times, fixed by immersing in a 4% paraformaldehyde solution at room temperature for 30 minutes, re-washed with PBS, and immunologically stained. The immunological staining was carried out by soaking the glass slide prepared above in PBS with a primary antibody to react overnight, followed by washing with PBS three times, and reacting with a secondary antibody in a dark room for one hour. After termination of the reaction, the glass slide was washed with PBS three times, mounted and observed under a fluorescent microscope.

As a result, the three-dimensional cell cluster formed from adipose stem cells according to the present invention exhibited a positive reaction with respect to CD29, CD34, KDR, CD31, and SMA, while exhibiting a negative reaction with respect to osteocalcin, nestin, and MAP-2. CD29 is a surface antigen which is specifically expressed on mesenchymal cells and epithelial cells, while CD34, KDR and CD31 are surface antigens specifically expressed on vascular endothelial cells. SMA is a cytoskeletal protein which is specifically expressed in smooth muscle cells. In addition, osteocalcin, nestin, and MAP-2 are proteins that are specifically expressed by bone cells and neural cells. Based on the above results, it was confirmed that a three-dimensional cell cluster formed by culturing adipose stem cells on a culture plate having a surface with a hydrophobic property are composed of vascular cells differentiated from the adipose stem cells.

Figure 4:
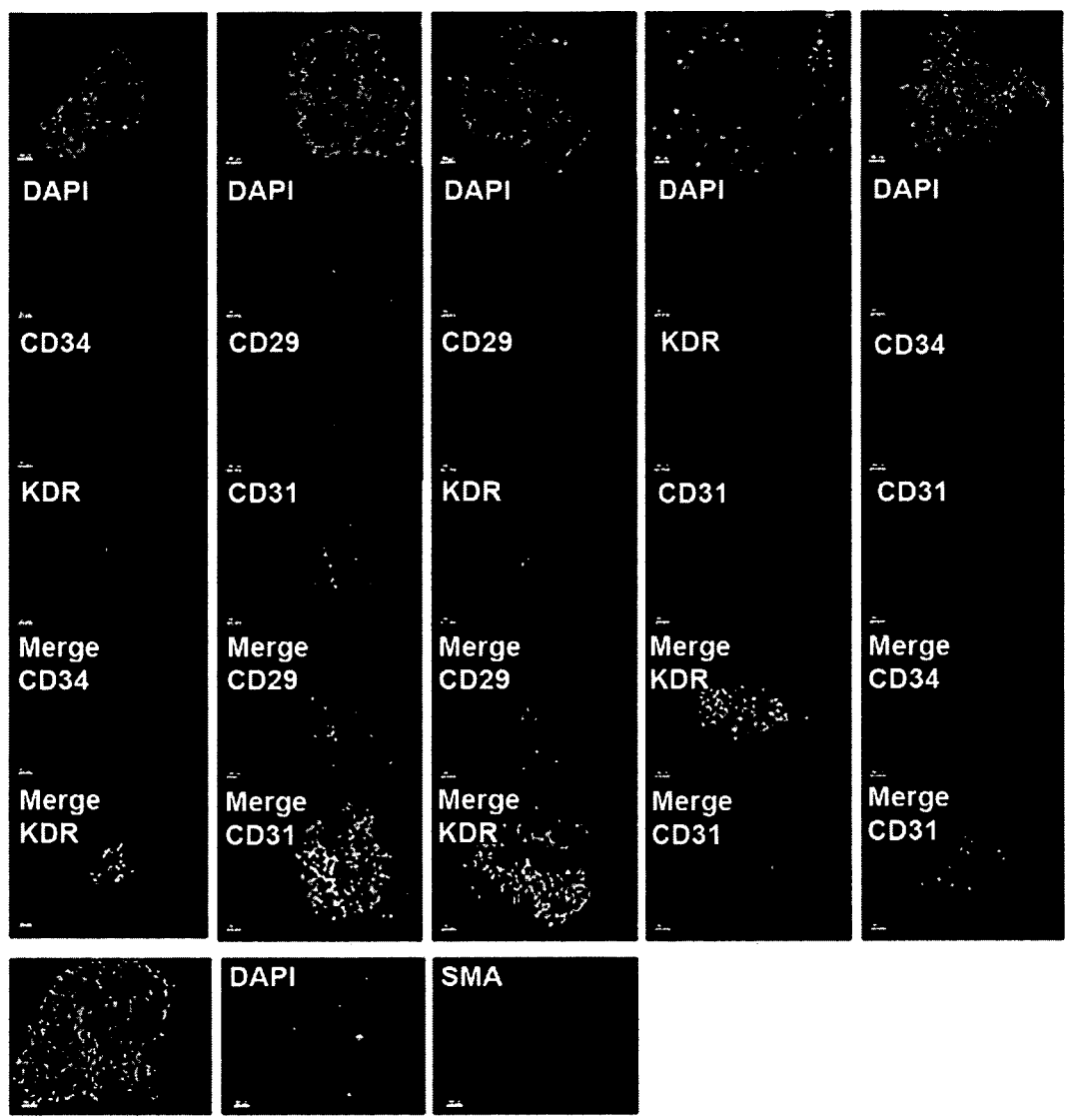
FIG. 4 shows the results from immunological staining of the three-dimensional cell cluster formed from adipose stem cells according to the present invention for CD29, CD34, KDR, CD31, and SMA.
Figure 5:
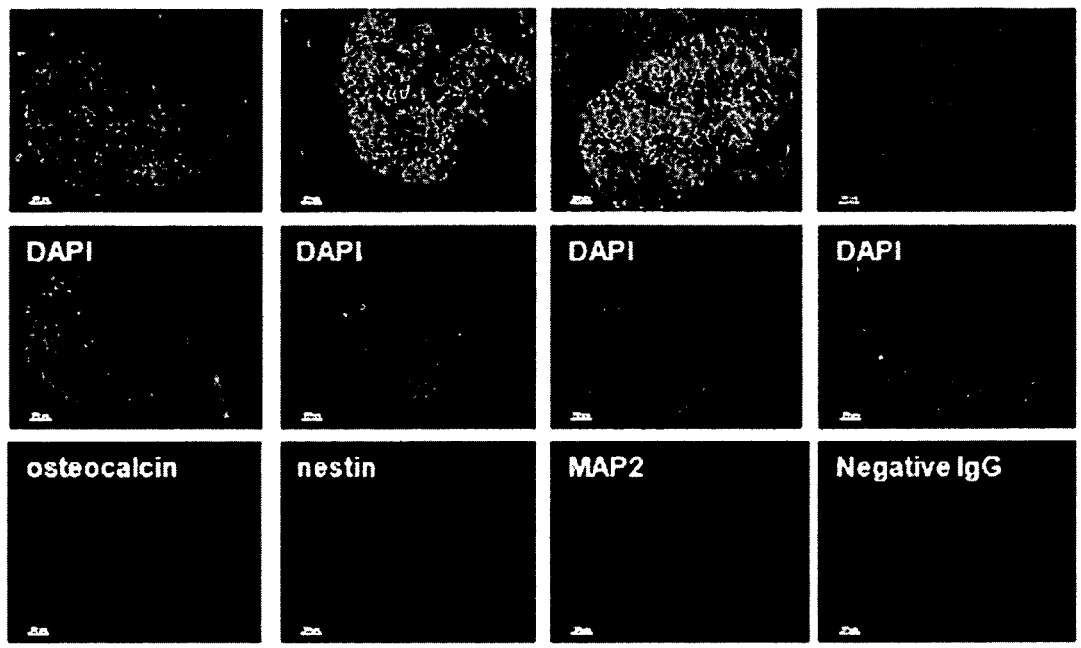
FIG. 5 illustrates the results from immunological staining of the three-dimensional cell cluster formed from adipose stem cells according to the present invention for osteocalcin, nestin, MAP-2, and mouse IgG as a negative control.

FIG. 4 shows the results from immunological staining of the three-dimensional cell cluster formed from adipose stem cells as described above with respect to CD29, KDR, CD31, and SMA. FIG. 5 shows the results from immunological staining of the same three-dimensional cell cluster with respect to osteocalcin, nestin, MAP-2, and mouse IgG as a negative control.

Example 4: Immobilization of a Growth Factor on a Hydrophobic Surface

In order to more effectively induce stem cell culture in the form of a cell cluster, growth factors having adherent activity to the stem cells were immobilized onto a culture plate having a hydrophobic surface. As the growth factor, fibroblast growth factor (FGF) that is expressed in the form of a recombinant protein with a maltose binding protein (MBP) as a polypeptide linker was used.

Specifically, a MBP-FGF recombinant protein having adherent activity to stem cells, where the amino terminal group of FGF is fused to the carboxyl terminal group of MBP, was expressed from an *Escherichia coli* transformant, i.e., K12 TB1 (pMAL-bFGF) (KCTC-11505BP), and then isolated and purified. The thus obtained MBP-FGF recombinant protein has an amino acid sequence of SEQ ID NO: 1. The MBP-FGF recombinant protein can be used in biochemical interactions with stem cells because the original FGF activity is maintained even though it is expressed as a recombinant protein with MBP and purified.

The MBP-FGF recombinant protein purified as above was filtered using a syringe (0.22 µm, Millex GV, Millipore) in a clean bench (Sanyo), then added in each well of a 24-well plate for non-tissue cell culture (NTCP, polystyrene, Falcon) in the amount of 100 µl at a concentration of 10 µg/ml, and left in the clean bench for 4 hours so as to be immobilized on the surface of the plate. Subsequently, the 24-well plate was washed with 200 µl PBS three times and some of the wells were further treated by adding 1% bovine serum albumin (BSA, Sigma) in the clean bench for two (2) hours in order to prevent the stem cells from binding to the MBP-FGF recombinant protein-immobilized well surface in a non-specific manner. Subsequently, the 24-well plate was washed with 200 µl PBS three times to prepare a 24-well plate on which the MBP-FGF recombinant protein was immobilized.

Example 5: Formation of a Cell Cluster on the Growth Factor-Immobilized Surface

The adipose stem cells prepared in Reference Example 1 were inoculated at $4\times10^4$ cells/cm$^2$ per well of a 24-well plate of which the MBP-FGF recombinant proteins prepared in Example 4 were immobilized on the surface. The adipose stem cells were cultured in a medium containing 10% FBS or serum-free DMEM/F12 at 37° C. for 3 days. After the three day culture, each well was observed under a phase-contrast microscope in order to confirm the formation of cell clusters of the adipose stem cells.

Figure 6:
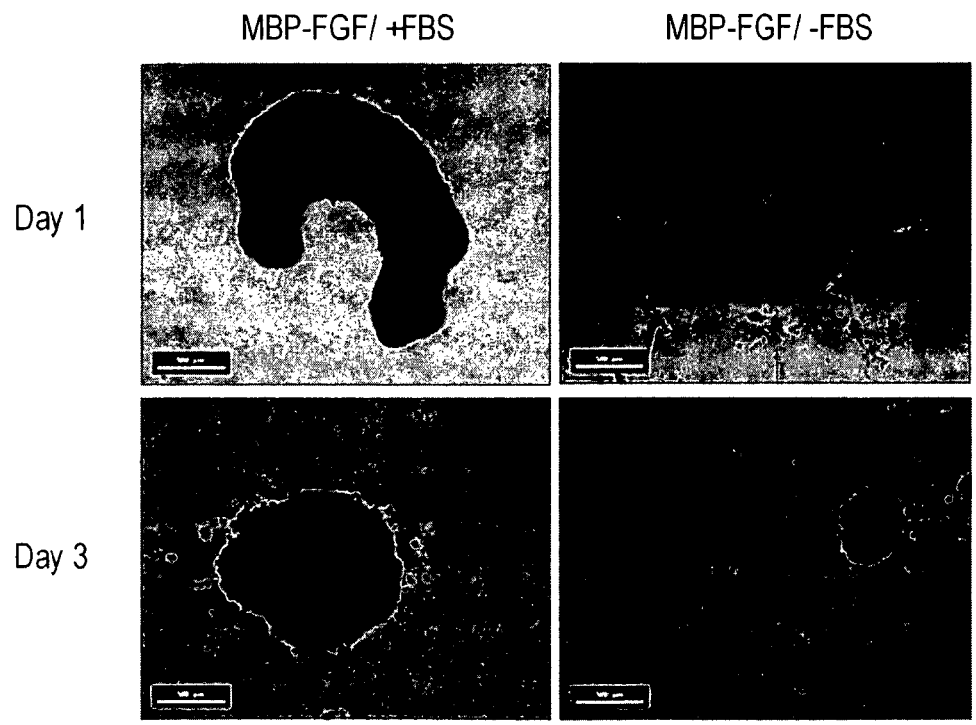
FIG. 6 is a photograph showing the three-dimensional cell cluster formed by culturing adipose stem cells in a FGF-immobilized culture plate according to the present invention, observed using a contrast-phase microscope under a magnification of 40.

As a result, as shown in FIG. 6, it was found that while at an early stage, the adipose stem cells proliferate while being adhered to the plate surface due to their biochemical interactions with the MBP-FGF recombinant protein having specific adherent activity to the adipose stem cells, the adipose stem cells were detached from the plate surface to form a three-dimensional cell cluster as their density increased. In particular, in 10% FBS containing DMEM/F12, the formation of a cell cluster began one day after the culture and three days later, a spherical cell cluster having a diameter of about 800 μM was formed. In serum-free DMEM/F12, three days after the culture, a cell cluster having a diameter of about 500 μm was formed. From the above results, it can be found that the immobilization of MBP-FGF recombinant proteins on the surface of a culture plate according to the present invention plays a key role in the formation of cell cluster of stem cells.

Example 6: Induction of Hypoxia Inside the Cell Cluster

Figure 7:
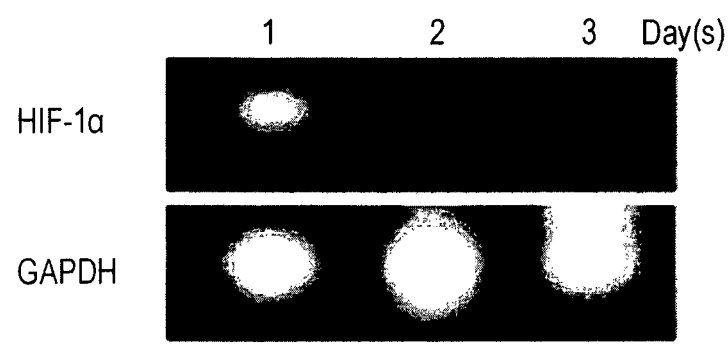
FIG. 7 shows the results from a RT-PCR analysis of HIF-1α expression in the three-dimensional cell cluster formed by culturing adipose stem cells in a FGF-immobilized culture plate according to the present invention.

In order to confirm that hypoxia inside the cell cluster was created by the formation of the cell cluster, the expression of HIF-1α (hypoxia inducible factor-1α) was examined by reverse transcriptase-PCR (RT-PCR). HIF-1α, a representative transcription factor that mediates the cellular response under hypoxic conditions, is known to be stabilized and activated under hypoxic conditions and to regulate the expression of several genes by binding to hypoxia response elements (HREs). Accordingly, the cell cluster was examined with respect to the expression of HIF-1α, which is indicative of hypoxia in the cell. First, stem cells were cultured on a MBP-FGF recombinant protein-immobilized well plate in a FBS containing DMEM/F12 medium. Total RNA was isolated from cell clusters obtained one, two, and three days after the culture using the TRIzol reagent (Invitrogen, USA) and was used as a template to synthesize cDNA using a Superscript II reverse transcriptase and an oligo (dT) primer. In order to confirm the expression of HIF-1α using the synthesized cDNA as a template, polymerization was carried out using a primer pair having SEQ ID NOS: 2 and 3 (HIF-1α sense: TGGACTCTCATCATCTGACC, HIF-1α anti-sense: CTCAAGTTGCTGGTCATCAG). As a result, as shown in FIG. 7, it was confirmed that hypoxia was created inside the cell cluster, based on the expression of HIF-1α in the cell cluster formed one day after culture.

Example 7: Increased Production of Angiogenic Stimulators in the Cell Cluster

Figure 8:
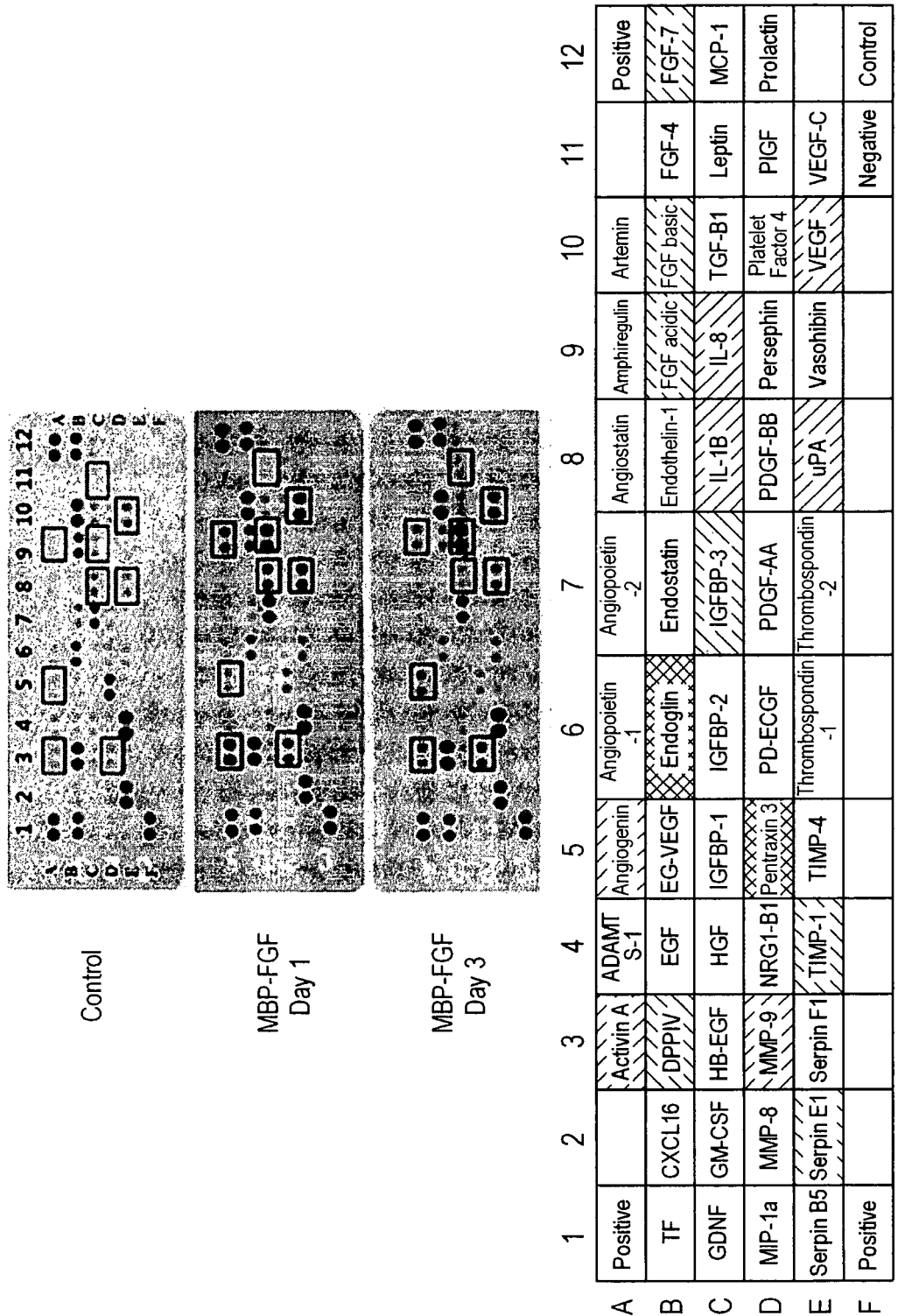
FIG. 8 illustrates the results from examining the production of angiogenic stimulators within the three-dimensional cell cluster formed by culturing adipose stem cells in a FGF-immobilized culture plate according to the present invention.

In order to confirm whether the hypoxia created in the cell cluster formed from stem cells enhances the production of angiogenic stimulators, the expression of angiogenesis related proteins was examined using an angiogenic protein analysis kit (Human Angiogenesis Array Kit, R&D Systems, Ltd.). Adipose stem cells cultured in a monolayer in a commercially available culture plate (control group) and those cultured in the form of a cell cluster in a MBP-FGF recombinant protein-immobilized culture plate as in Example 5 above (Days 1 and 3) were harvested. Every $5 \times 10^6$ harvested cells were washed with PBS several times and then 500 μl of the lysis buffer were added respectively. These cells were mixed using a pipette several times and subject to a reaction at 4° C. for 30 minutes to obtain a cell homogenate. The obtained cell homogenate was subject to centrifugation (Combi-514R, Hanil) at 14,000×g for 5 minutes to separate the supernatant in which proteins are dissolved and the concentration of the proteins was quantified. The supernatant separated above was allocated in an amount of 0.5 ml to each well of the 4-well multi-dish within the angiogenic protein analysis kit, followed by a reaction in the rocking platform for one (1) hour with the addition of 2 ml of blot buffer and nitrocellulose membranes. On the nitrocellulose membrane, fifty-five (55) angiogenesis-related protein antibodies were blotted as shown in FIG. 8. After the multi-dish was washed several times, 1.5 ml of biotin-conjugated antibodies were added to react at 4° C. for about twelve (12) hours. After the completion of the reaction, the multi-dish was washed several times, followed by the addition of streptavidin-horseradish and 1.5 ml of chemiluminescent detection reagents and a reaction in the darkroom for one (1) hour. After one hour, expression of the angiogenesis related proteins was observed using an image reader LAS-3000 (Fujifilm, Tokyo, Japan).

As a result, as shown in FIG. 8, in the cell cluster of adipose stem cells formed from the MBP-FGF recombinant protein-immobilized culture plate according to the present invention, an overexpression of various angiogenesis-related proteins including VEFG, angiogenin, and IL-8 was detected, starting from one (1) day after the culture. The above results indicate that if stem cells are cultured in the form of a three-dimensional cell cluster according to the present invention, the formation of the cell cluster reduces the transmission of oxygen to the inside of the cluster, by which hypoxia is created, and thus the production of various angiogenic stimulators affecting the differentiation of vascular endothelial cells is induced.

Example 8: Differentiation of Stem Cells in the Cell Cluster into Vascular Cells As in Example 5, adipose stem cells were cultured in a culture plate on which a MBP-FGF recombinant protein was immobilized at a concentration of $4 \times 10^4$ cells/cm$^2$ and the formed cell cluster was harvested. The harvested cell cluster was fixed at −70° C. using an OCT compound and then cut into a thickness of 4 μm using a microtome. The fragment was fixed on a glass slide and immunologically stained. The immunological staining was carried out by soaking the glass slide prepared above in PBS with a primary antibody to react overnight, followed by washing with PBS three times, and reacting with a secondary antibody in a dark room for one hour. After termination of the reaction, the glass slide was washed with PBS three times, mounted and observed using flow cytometry.

As a result, a cell cluster of adipose stem cells formed in a MBP-FGF recombinant protein-immobilized culture plate according to the present invention exhibited a positive reaction with respect to CD29, CD34, KDR, CD31, and SMA, while exhibiting a negative reaction with respect to osteocalcin, nestin, and MAP-2. CD29 is a surface antigen which is specifically expressed on mesenchymal cells and epithelial cells, while CD34, KDR and CD31 are surface antigens specifically expressed on vascular endothelial cells. SMA is a cytoskeletal protein which is specifically expressed in smooth muscle cells. In addition, osteocalcin, nestin, and MAP-2 are proteins that are specifically expressed by bone cells and neural cells. Based on the above results, it was confirmed that a three-dimensional cell cluster formed by culturing adipose stem cells on a FGF-immobilized culture plate are composed of the vascular cells differentiated from the adipose stem cells.

Figure 9A:
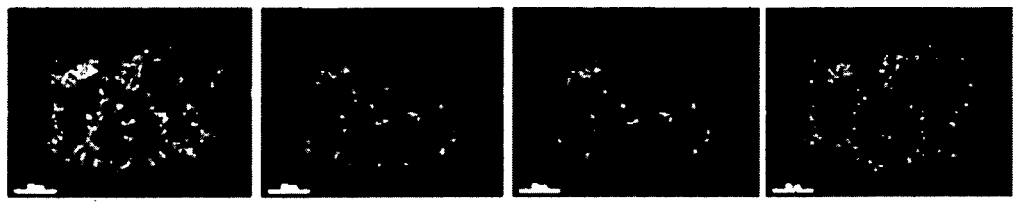
FIG. 9a shows the results from immunological staining of the cell cluster formed from culturing adipose stem cells in a medium with serum on a growth factor-immobilized culture plate according to the present invention for CD29, CD34, KDR, and CD31.
Figure 9A:
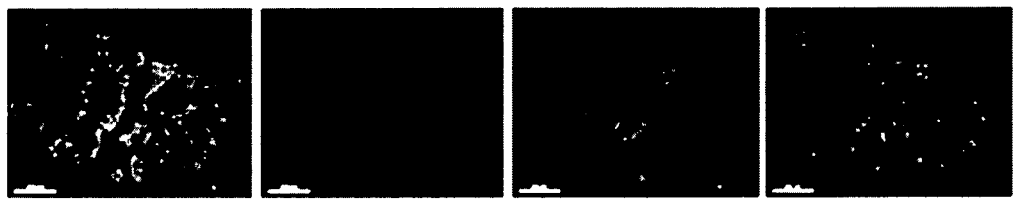
Figure 9A:
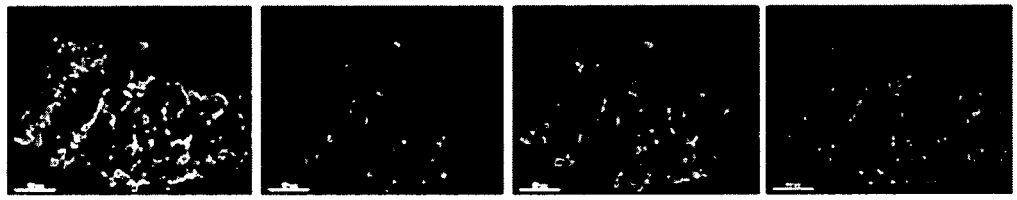
Figure 9B:
FIG. 9b illustrates the results from immunological staining of the cell cluster formed from culturing adipose stem cells in a medium with serum on a growth factor-immobilized culture plate according to the present invention for SMA, nestin, and MAP-2.
Figure 9B:
Figure 9B:
Figure 10:
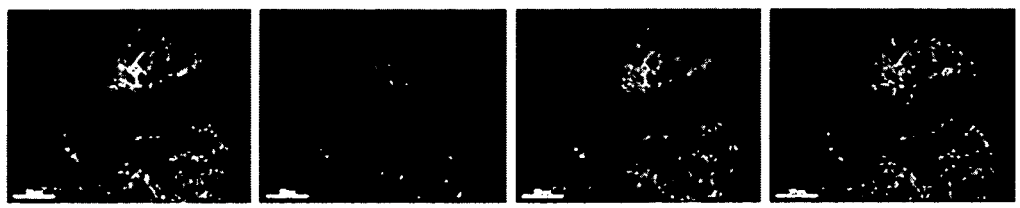
FIG. 10 shows the results from immunological staining of the cell cluster formed from culturing adipose stem cells in a serum-free medium on a growth factor-immobilized culture plate according to the present invention to CD29, CD34, KDR, and CD31.
Figure 10:
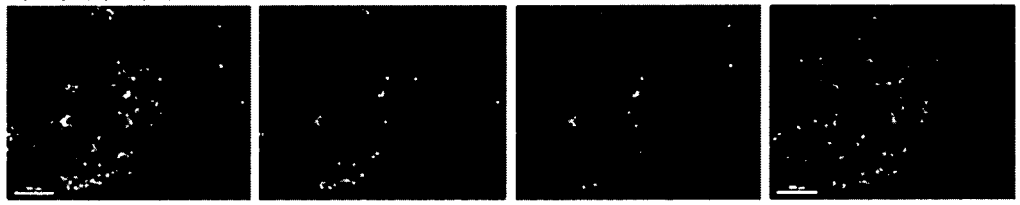
Figure 10:
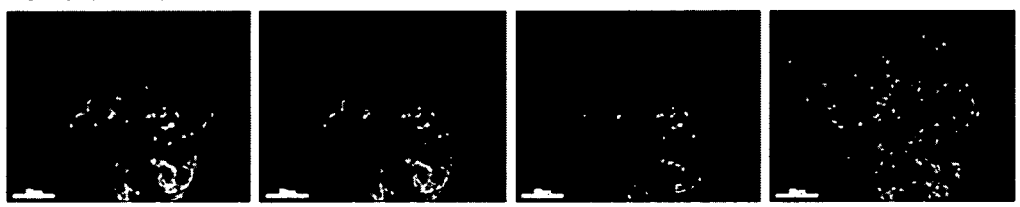

FIG. 9a shows the results from CD29, CD34, KDR and CD31 immunological staining of the cell cluster formed from adipose stem cells in the presence of a serum containing medium on a growth factor-immobilized culture plate according to the present invention. FIG. 9b shows the results from immunological staining of the same cell cluster to SMA, nestin, and MAP-2. FIG. 10 shows the results from CD31, CD34 and KDR immunological staining of the cell cluster formed from adipose stem cells in the presence of a serum-free medium on a growth factor-immobilized culture plate according to the present invention.

Example 9: Evaluation of Angiogenesis by In Vivo Transplantation of the Cell Cluster In order to evaluate the in vivo angiogenesis effect of the cell cluster composed of the vascular endothelial cells differentiated from stem cells according to the present invention, $1 \times 10^6$ undifferentiated adipose stem cells isolated in Reference Example 1 or vascular cells differentiated from adipose stem cells constituting the cell cluster obtained in Example 5 were added in a solution comprising 500 µl Matri-gel (BD Biosciences, main components: laminine, collagen type 4, heparin sulfate proteoglycans (HSPG), and entactin/nidogen)) and 6 µl fibrinogen (final concentration 2 mg/ml; Green Cross) to obtain a mixture, and then 2.5 µl thrombin (0.4 U; Green Cross) was added to the mixture. The mixture prepared in the form of a gel was subcutaneously injected to four (4) week-old male BALB/c-nude mice (purchased from Central Lab. Animal Inc.) (see FIG. 11). The control group was injected with only 500 µl of phosphate buffered saline (PBS). After the injection, the injection of the gel into the mice was confirmed with naked eyes and three weeks later, the mice were euthanized using nitrogen gas and then their skin was incised to recover the gel. The gel was examined to confirm angiogenesis by visual observation, immunological staining, and confocal microscopy.

Figure 11:
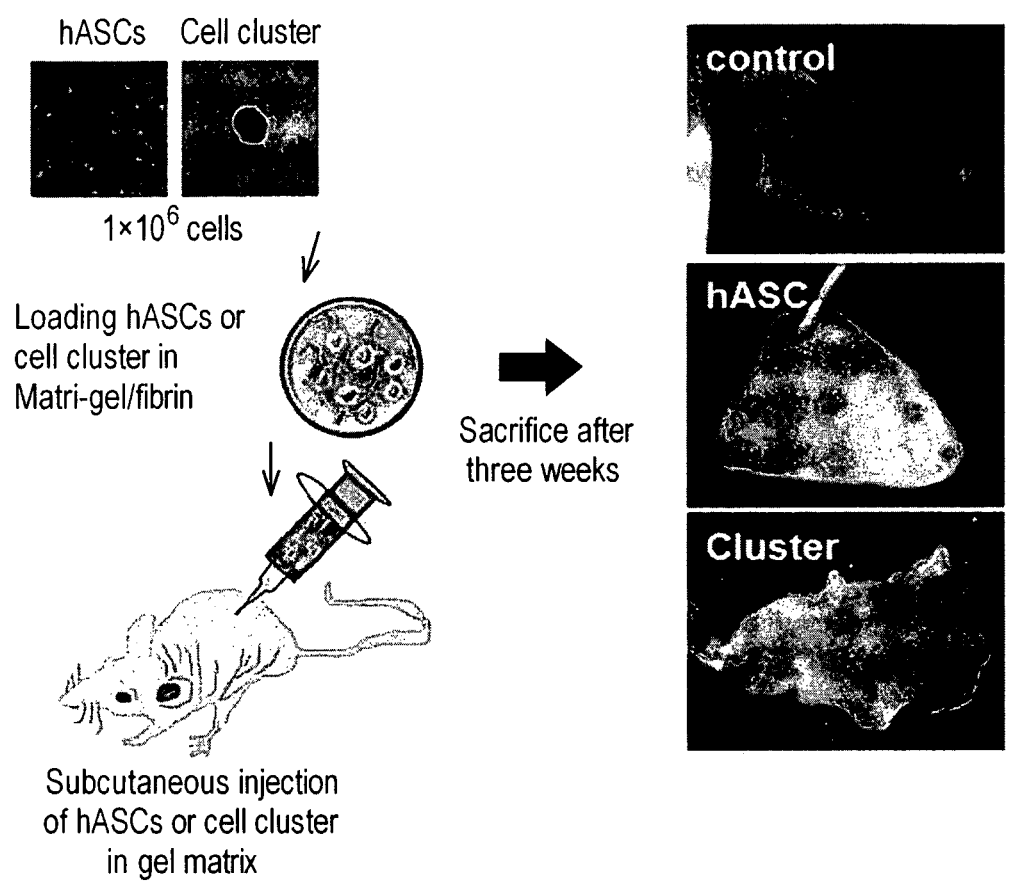
FIG. 11 is a schematic diagram showing in vivo transplantation of the three-dimensional cell cluster formed from culturing adipose stem cells according to the present invention in nude mice and the results from a naked eye observation of the tissues removed from the mice three weeks after transplantation.

As illustrated in FIG. 11, when observed with naked eyes, in the case where only a solution of Matri-gel/fibrin without injected cells was transplanted in the mice, the recovered gel was found to remain translucent. By comparison, when a solution of Matri-gel/fibrin injected with undifferentiated adipose stem cells was transplanted, the recovered gel was opaque and some angiogenesis was observed. In the case where a solution of Matri-gel/fibrin injected with a cell cluster composed of the vascular cells differentiated from stem cells according to the present invention was transplanted, many red colored blood vessels were formed.

Figure 12:
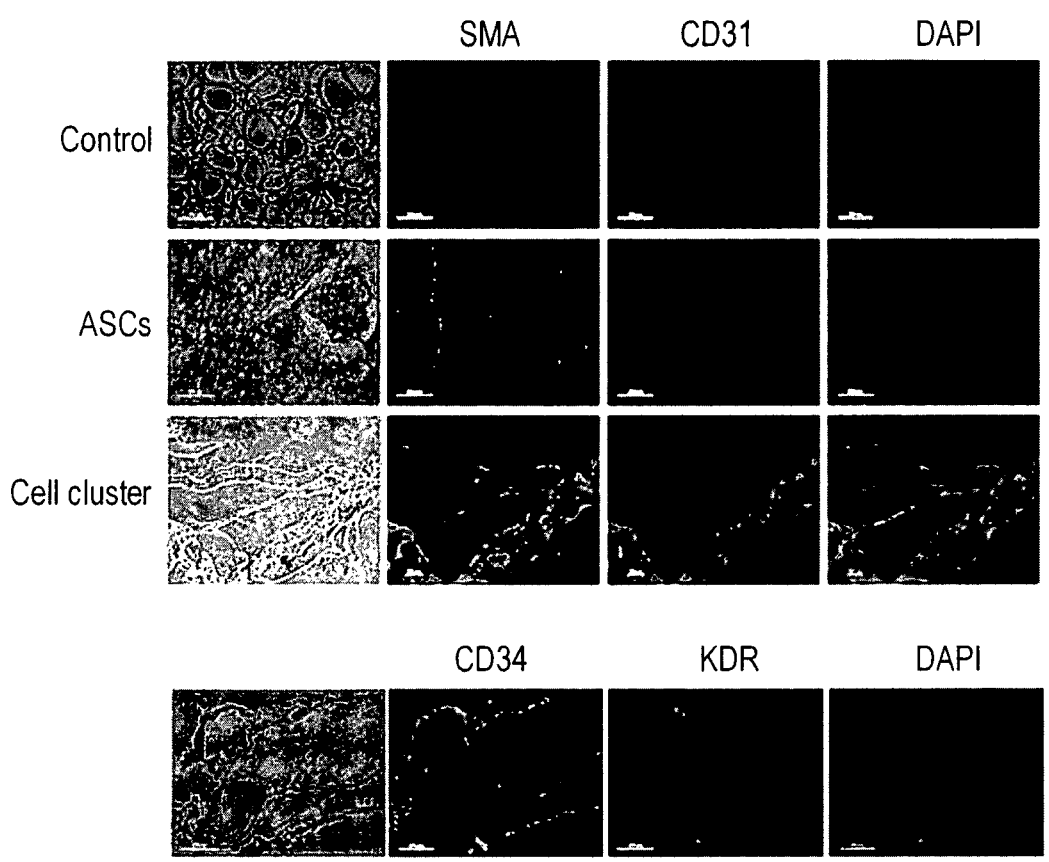
FIG. 12 shows the results from immunological staining of the tissues of FIG. 11 for SMA, CD31, CD34, and KDR.

FIG. 12 shows the results from the immunological staining of tissues removed from the nude mice which were injected with the Matri-gel/fibrin gel, using anti-human CD31, CD34, KDR, and SMA antibodies. As a result, where only a solution of Matri-gel/fibrin was transplanted, neither CD31 nor SMA was stained. When a solution of Matri-gel/fibrin injected with undifferentiated adipose stem cells was transplanted, there were a few cells which were positive to CD31 and SMA but no blood vessel-like structure was observed. On the other hand, in the case where a solution of Matri-gel/fibrin injected with a cell cluster composed of the vascular cells differentiated from stem cells according to the present invention was transplanted, the tissues were positive to all of CD31, CD34, KDR, and SMA, and blood vessel-like and tubular-shaped channels were observed. The above results indicate that the blood vessels formed in the nude mice were derived from a cell cluster composed of the vascular cells differentiated from stem cells, which was transplanted on the site where the blood vessels were formed.

Example 10: Evaluation of Angiogenesis in Ischemic Rat Models of the Cell Cluster In order to evaluate whether the cell cluster composed of the vascular cells differentiated from stem cells according to the present invention exhibits a therapeutic effect for regeneration of blood vessels in ischemic animal models, Sprague-Dawley rats were anesthetized by ether inhalation. After shaving the lower legs and a skin incision, occlusion of the femoral artery was carried out to create ischemic conditions. Four (4) hours after the occlusion of the femoral artery in the lower legs, undifferentiated adipose stem cells isolated in Reference Example 1 or vascular cells differentiated from adipose stem cells constituting the cell cluster obtained in Example 5 were injected in the leg muscles of eight (8) ischemic rats at intervals of 0.5 cm diameter ($5 \times 10^6$ cells per interval). As the control group, four (4) rats were injected with only PBS. At one (1) day, two (2) weeks, and four (4) weeks after the injection, the rats were examined for hypothermia. After four weeks, blood flow was imaged using a laser Doppler and quantitatively measured. After that, the rats were euthanized using nitrogen gas and then their lower legs under ischemia were removed. The removed legs were examined by immunological staining for confirmation of angiogenesis.

Figure 13:
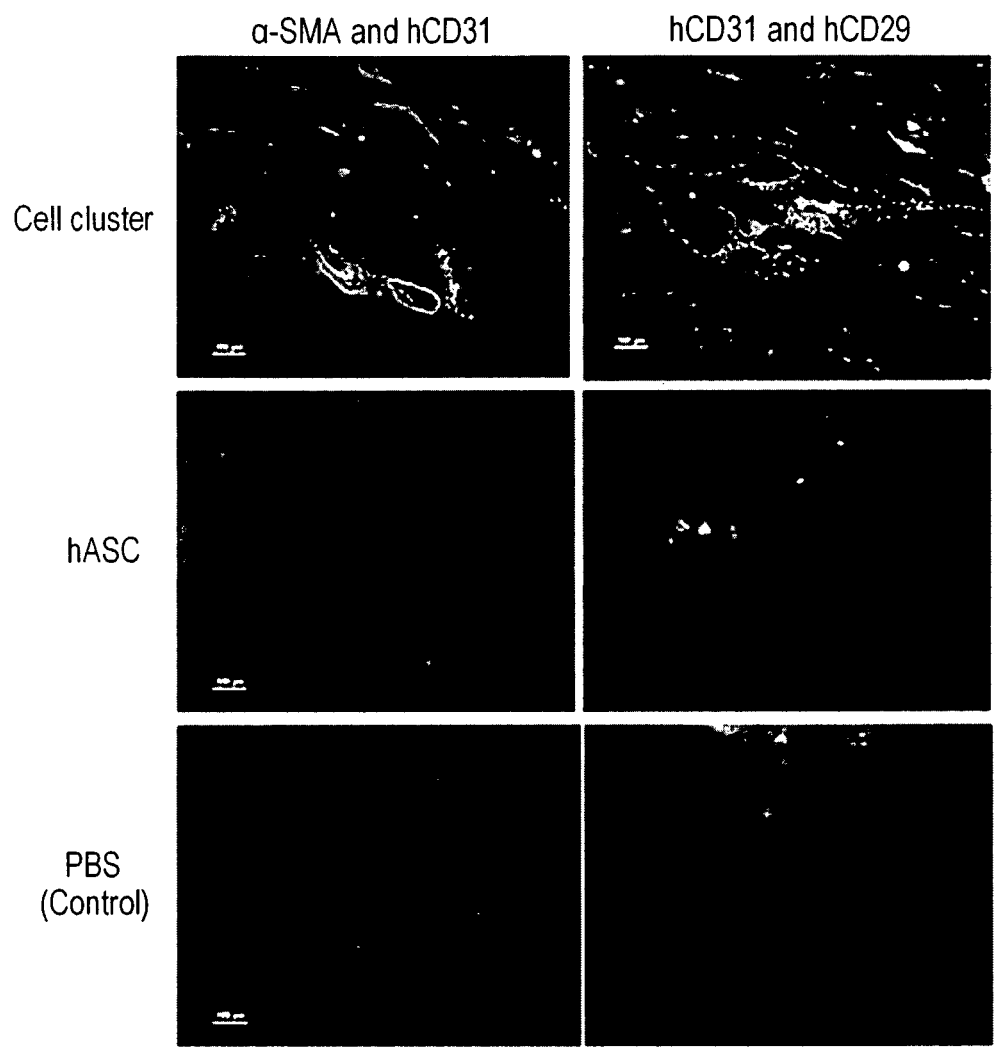
FIG. 13 illustrates the results of immunological staining of the ischemic tissues in ischemic rat models transplanted with the cell cluster composed of vascular cells differentiated from adipose stem cells according to the present invention for SMA, CD29 and CD31.
Figure 14:
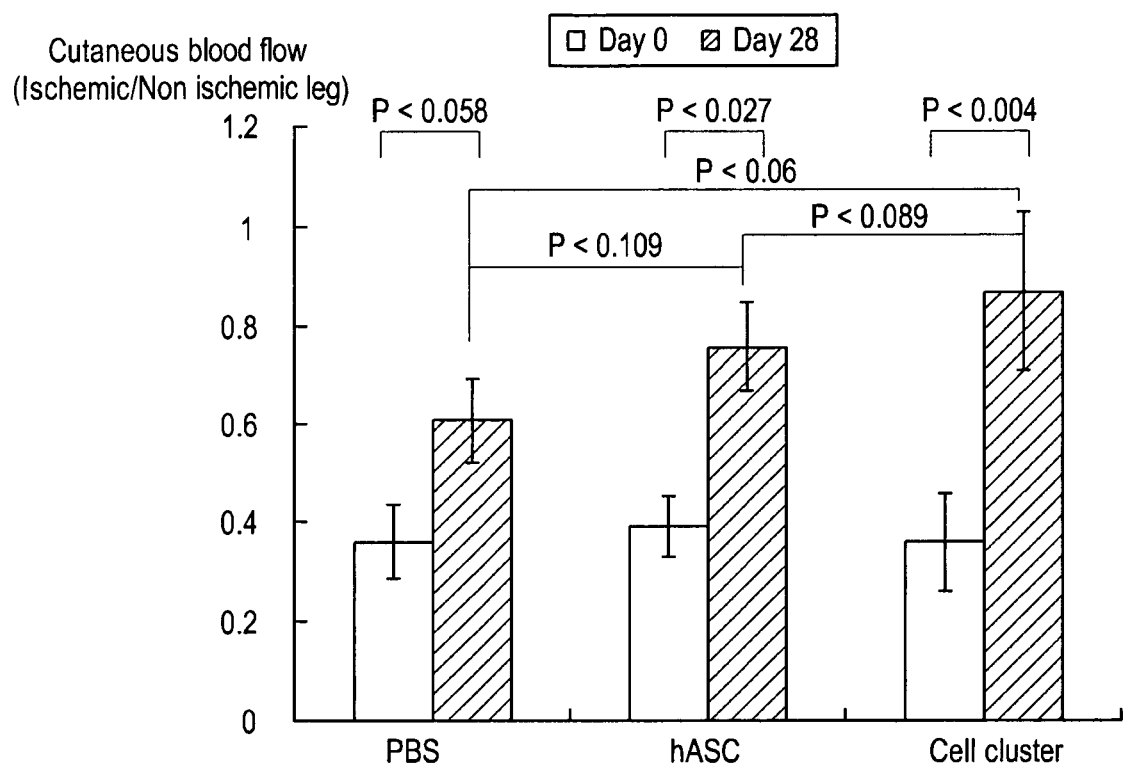
FIG. 14 is a graph showing the quantification of blood flow in the hind limb of ischemic rat models transplanted with the cell cluster composed of vascular cells differentiated from adipose stem cells according to the present invention.

As shown in FIG. 13, only the case where a cell cluster composed of the vascular cells differentiated from stem cells according to the present invention was transplanted was positive staining to anti-human CD31, SMA, and CD29 observed. As illustrated in FIG. 14, it can be found that in the case where a cell cluster composed of the vascular cells differentiated from stem cells according to the present invention was transplanted, the blood flow increased as compared to the control group or the case where adipose stem cells were transplanted. The above results indicate that a cell cluster composed of the vascular cells differentiated from stem cells according to the present invention can be effectively used in the treatment for the regeneration of ischemic lower limbs.

While the invention has been described in detail with respect to specific parts of the invention, it will be apparent to those skilled in the art that such descriptions are nothing more than exemplary embodiments of the invention and thus that the scope of the invention is not limited thereto.

What is claimed:

1. A method of differentiating adipose stem cells into vascular endothelial cell clusters for the induction of angiogenesis comprising:
   applying adipose stem cells to a culture plate having a hydrophobic surface and a growth factor immobilized thereon at a concentration of $1 \times 10^4$ to $3 \times 10^5$ cells/cm$^2$, wherein said growth factor is fibroblast growth factor (FGF), and wherein the hydrophobic surface is selected from the group consisting of a silanized surface, a hydrocarbon coated surface, a polymer surface and a metal surface;
   allowing the stem cells to adhere to the surface of the plate by physical attraction of the stem cells to the hydrophobic surface and by biological attraction of the stem cells to the growth factor;
   culturing the stem cells in a culture medium while being attached to the surface of the culture plate, and subsequently forming a three-dimensional cell cluster detached from the culture plate and floating in the culture medium, wherein the culture medium is a mixture of DMEM, Ham's F12, and serum; and
   culturing the three-dimensional cell cluster in the culture medium to induce differentiation of the stem cells into vascular endothelial cells.

2. The method according to claim 1, wherein said polymer is selected from the group consisting of polystyrene, polymethylmethacrylate (PMMA), polyethylene terephthalate (PET), polyvinylchloride (PVC), polyethylene (PE), polypropylene (PP), polytetrafluoroethylene (PTFE), poly(L-lactic acid) (PLLA), poly(D,L-lactic acid) (PDLLA), poly(glycolic acid) (PGA), poly(caprolactone) (PCL), poly(hydroxyalkanoate), polydioxanone (PDS), polytrimethylencarbonate, and copolymers.

3. The method according to claim 1, wherein said metal is selected from the group consisting of stainless steel, titanium, gold, and platinum.

4. The method according to claim 1, wherein said growth factor is immobilized on the surface of the culture plate using a polypeptide linker in the form of a polypeptide linker-growth factor recombinant protein in which an amino terminal group of the growth factor is fused to a carboxy terminal group of the polypeptide linker.

5. The method according to claim 4, wherein said polypeptide linker is selected from the group consisting of maltose-binding protein (MBP), hydrophobin, and hydrophobic cell penetrating peptides (CPPs).

6. The method according to claim 4, wherein, in the polypeptide linker-growth factor recombinant protein, an amino terminal group of a fibroblast growth factor (FGF) is fused to a carboxyl terminal group of a maltose binding protein (MBP) and wherein said polypeptide linker-growth factor recombinant protein has an amino acid sequence of SEQ ID NO: 1.

7. The method according to claim 1, wherein the cell cluster has a diameter of 400 μm to 1 mm.

* * * * *

SEQUENCE LISTING

<160> NUMBER OF SEQ ID NOS: 3

<210> SEQ ID NO 1

<211> LENGTH: 389
<212> TYPE: PRT
<213> ORGANISM: Artificial Sequence
<220> FEATURE:
<223> OTHER INFORMATION: MBP-FGF recombinant protein

<400> SEQUENCE: 1

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380
```

```
Glu Gly Arg Ile Ser
385

<210> SEQ ID NO 2
<211> LENGTH: 20
<212> TYPE: DNA
<213> ORGANISM: Artificial Sequence
<220> FEATURE:
<223> OTHER INFORMATION: HIF-1a sense primer

<400> SEQUENCE: 2
tggactctga tcatctgacc                                              20

<210> SEQ ID NO 3
<211> LENGTH: 20
<212> TYPE: DNA
<213> ORGANISM: Artificial Sequence
<220> FEATURE:
<223> OTHER INFORMATION: HIF-1a antisense primer

<400> SEQUENCE: 3
ctcaagttgc tggtcatcag                                              20
```